US005523745A

United States Patent [19]
Fortune et al.

[11] Patent Number: 5,523,745
[45] Date of Patent: Jun. 4, 1996

[54] TONGUE ACTIVATED COMMUNICATIONS CONTROLLER

[75] Inventors: Daniel Fortune, Palo Alto; John E. Ortiz, East Palo Alto; Hien N. Tran, Santa Cruz, all of Calif.

[73] Assignee: Zofcom Systems, Inc., Palo Alto, Calif.

[21] Appl. No.: 233,611

[22] Filed: Apr. 18, 1994

Related U.S. Application Data

[63] Continuation of Ser. No. 774,675, Oct. 11, 1991, abandoned, which is a continuation-in-part of Ser. No. 285,771, Dec. 16, 1988, abandoned.

[51] Int. Cl.$^6$ ..................................................... H04Q 7/00
[52] U.S. Cl. ............................... 340/825.19; 340/825.69; 340/825.56
[58] Field of Search ......................... 340/825.19, 825.69, 340/825.72, 825.64, 825.56, 407.2; 341/21, 22, 176; 455/100, 41; 400/87; 434/112, 113; 128/774, 777; 200/DIG. 2, 513; 381/70; 343/866

[56] References Cited

U.S. PATENT DOCUMENTS

| | | | |
|---|---|---|---|
| 4,243,846 | 1/1981 | Lenearts et al. | 361/397 |
| 4,263,485 | 4/1981 | Corwin | 200/292 |
| 4,310,002 | 1/1982 | Takinishi | 128/777 X |
| 4,334,542 | 6/1982 | Takinishi et al. | 128/777 |
| 4,353,064 | 10/1982 | Stamm | 340/825.69 |
| 4,482,895 | 11/1984 | Weinberg | 340/825.69 |
| 4,539,699 | 9/1985 | Katz et al. | 381/70 |
| 4,605,927 | 8/1986 | Katz et al. | 340/825.19 |
| 4,616,213 | 10/1986 | Danish | 341/21 |
| 4,629,924 | 12/1986 | Lauks et al. | 455/100 |
| 4,733,215 | 3/1988 | Memmola | 340/825.72 X |
| 5,212,476 | 5/1993 | Maloney | 340/825.19 |
| 5,233,662 | 8/1993 | Christensen | 381/70 |

*Primary Examiner*—Donald J. Yusko
*Assistant Examiner*—Edwin C. Holloway, III
*Attorney, Agent, or Firm*—Haynes & Davis

[57] ABSTRACT

A tongue activated communications controller for use by disabled or other persons to control a wide variety of devices, and which includes a dental appliance fitted to the user's palate, and a keyboard with a plurality of tongue activatable switches for generating a signal depending upon which switch has been selected, and upon the status of a battery voltage level. The communications controller includes a radio frequency transmitter which uses magnetic flux linkage for transmitting the signal. The communications controller further includes a receiver for converting the transmitted signal into digital form, and also includes a micro-processor based controller unit for processing the received data, and for communicating with the attached devices which the user wishes to control. Data is sent from the transmitter using a fixed transmission time, digital pulse code modulation technique to achieve ultra low power consumption in the transmitter. The controller unit processes the encoded data signal from the receiver by measuring and storing the intervals between level transitions, and then by processing these intervals in non-real time.

21 Claims, 15 Drawing Sheets

TIMER  140

PULSE LINE
NO SWITCH  142

PULSE LINE
SW1  144

PULSE LINE
SW1 & CARRIER  145

PULSE LINE
SW2  146

PULSE LINE
SW2 & CARRIER  147

PULSE LINE
SW3  148

TIMER

PULSE LINE
NO SWITCH

PULSE LINE
SW1

PULSE LINE
SW1 & CARRIER

PULSE LINE
SW3

PULSE LINE
SW3 & CARRIER

TIMER

PULSE LINE
NO SWITCH

PULSE LINE
SW1

PULSE LINE
SW1 & CARRIER

PULSE LINE
SW3

PULSE LINE
SW3 & CARRIER

TONGUE ACTIVATED COMMUNICATIONS CONTROLLER

CROSS-REFERENCE TO OTHER APPLICATIONS

This is a file wrapper continuation application of patent application Ser. No. 07/774,675, filed Oct. 11, 1991, now abandoned. Patent application Ser. No. 07/774,675 is a continuation-in-part application of patent application Ser. No. 07/285,771, filed Dec. 16, 1988 now abandoned.

BACKGROUND OF THE INVENTION

1. Field of the Invention

This invention relates to the field of communications controllers and more particularly to the field of such controllers which are activated with a user's tongue.

2. Previous Art

A significant portion of persons who do not have the use of their limbs are isolated from daily functioning in society. Some of these persons may have suffered traumatic injuries to their spinal cord, such as during automobile accidents or sport injuries and the like; others may have had diseases of the neuromuscular and central nervous system. In these types of diseases, cognitive function most often remains intact. It has been found that often these pathologies do not affect the function of the user's tongue. The tongue remains accessible as a communications link after all limb control has been lost, even in such progressive neuromuscular diseases, such as multiple sclerosis.

The number of such disabled people is increasing in the general population. Thus, there is an increased need for new devices that allow the disabled person to work and to have a near-normal lifestyle. With a faster and more aesthetically acceptable communications controller, it is possible for the disabled person to become a productive part of society. There has been a great amount of recent development in this area, particularly in the area of computer controllers for operating mechanical devices.

Current devices exist for hands free computer input. These devices include a mouth stick controller which is a device clenched in the user's teeth and operated by gross head motions to perform various mechanical tasks. This device is utilized primarily by high level quadriplegics and can be wielded with adequate proficiency after some practice. However it requires a high degree of mobility to accomplish specific tasks and is often awkward to use and leads easily to deterioration of teeth and oral occlusion. Additionally, a mouth stick controller has the limitation that the patient must be in extremely close proximity, in fact a mouth stick controller extends from the mouth to the device being operated.

Voice recognition systems are known. However, further refinement is necessary to produce a reliable method of data communication even for a person having an unimpaired voice. In many cases, quadriplegics have partial paralysis of the diaphragm and larynx. Their speech articulation and volume are severely hampered. Therefore, voice recognition systems, which require good articulation and volume, are not well suited to a broad range of physically impaired persons. Additionally, voice recognition systems present difficulty in environments where multiple users coexist.

Other devices proposed to assist the disabled person include many forms of single switch computer control. This type of control is slow to operate and requires many levels of programming. Typically, a single switch actuation device requires an action such as "sip" and "puff" breathing, eyebrow motion, or chin movements to control or to operate a computer, to actuate an environmental control or to achieve personal mobility. Disabled persons with a great degree of mobility and who have a capacity to operate more than one switch desire increased and faster access to a computer. Currently, single switch driven software does not achieve the desired speed that can be obtained by multiple switch inputs.

Another relevant device is an ultra-sonic head controller. This device is limited to the user that is able to produce at least small and precise head movements necessary for keying a computer via ultra-sonic position detectors. The computer recognizes the position of the head and deviations in head positions are interpreted as an analog signal. An example of an ultrasonic device is the Personics View Control System (VCS), which is currently commercially available. The Personics system includes three ultra sonic transducers housed in a headset to receive a signal transmitted from a control unit. By comparing the signal received at three points on the headset, changes in the angle and rotation of the head are tracked.

Yet another device which is designed for persons of limited mobility is an eye switch apparatus which is an infrared emitter and detector pair mounted on standard eye-glasses. This system operates by emitting small, low power, infrared beams. The reflectivity of the surfaces in front of the emitter can be sensed. For example, when the eyelid opens or closes, an electronics unit activates a relay which serves as a switch. Virtually any body surface can reflect the beam, giving a wide range of threshold levels and possible methods of operation. However, there is a distinct lack of speed in the use of such a device and there is the disadvantage of triggering this type of device unintentionally, such as during normal eye blinking.

The devices currently known are quite limited in the variety of devices they can control. Additionally, presently known devices require physical movements from the disabled user that may not be possible. What is needed is a device which can be used by a large number of persons having limited mobility and which can operate a broad range of devices. The device must not require difficult physical movements for persons suffering from progressive neuromuscular disorders and quadriplegia due to spinal injuries and the device should be aesthetically pleasing.

Low power frequency modulated (FM) radio transmitters are well known in the field of system application controllers and in the communications field. For example, residential wireless telephones, garage door openers, remote controlled toys and various games are applications of frequency modulated radio transmitters to control applications in and around the home.

Presently, miniaturization allows the same FM technology which is used in the home to be used in an intra-oral transmitter intended to help the disabled. However, some difficulties remain. Included in these difficulties are: (1) the need to use carrier frequencies of approximately 88 Mhz to reduce the size of the electric field antenna; (2) the need to continuously transmit the carrier frequency; and (3) limitations on the size of the battery imposed by the small size of these devices. Problems (1) and (2), above, result in excessive battery drain, while problem (3) places a limit on battery life.

The existing devices do not employ some means of communicating to the user the fact that battery output is marginal. This combination of high battery drain and non-reporting of battery status creates a reliability problem. At least one device uses a circuit which turns off the carrier frequency and resets the logic circuits when no user operable switch is activated. But this circuit still requires power to perform its function and thus battery drain remains a major problem.

The use of high frequency, electric field transmission also creates an additional problem: interference between other users who are in the immediate vicinity (20 to 1000 feet). Some applications embed an ID code in every transmission to protect against such interference. This approach increases the battery drain, and lacks a practical method of changing the ID code to prevent interference from a user having the same code.

SUMMARY OF THE INVENTION

It is a general object of this invention to provide a tongue activated communications controller which enables persons of limited mobility to operate various devices reliably.

It is a further object of this invention to provide such a tongue activated communications controller which is well suited for use by persons having quadriplegia due to spinal cord injuries and neuromuscular disorders.

It is yet a further object of this invention to provide a tongue activated communications controller which has an improved battery life, and a shelf life approaching that of the battery itself.

It is an additional object of this invention to provide a tongue activated communications controller which has decreased size and weight, improved reliability and safety, can be used in numerous applications by disabled and non-disabled persons, and is resistant to interference from adjacent users.

In accordance with the above objects, a tongue activated communications controller in accordance with this invention comprises:

an intra-oral transmitting assembly including:
  a two sided circuit board, the first side having electronic means for transmitting an electrical signal and the second side having a keyboard with a plurality of tongue activatable positions, the activated positions encode a signal for transmission; and a wireless transmitter having an inductor defining an antenna for enhanced transmission of the encoded signals, the inductor having one or more windings around the perimeter of the printed circuit board; and receiving means for receiving the encoded signals from the transmitting assembly including computing means for decoding the encoded signals and for forming a set of instructions for operating a device from the decoded signals and means for sending the instructions to the device for operation.

In another preferred embodiment the tongue activated communications controller comprises:

an intra-oral transmitting assembly including:
  a keyboard having a plurality of tongue-activated switches, each switch having an interval of switch activation defined by the depression of the switch; an encoding means for receiving input from all the tongue-activated switches and, during an interval of switch activation, for generating a waveform which is a function of the specific switch activated; and
  a magnetic coupling means for receiving the waveform from the encoding means and, during the interval of switch activation, for generating a time-varying magnetic field whose properties are a function of the waveform and a receiving means for receiving the time-varying magnetic field generated by the intra-oral transmitting assembly, the receiving means including:
  a decoding means for converting the received time-varying magnetic field into a waveform which is a function of the specific switch activated and a control means for converting the waveform of the decoding means into appropriate action, whereby upon tongue activation of one of the switches an appropriate action is taken.

In another preferred embodiment, the intra-oral transmitting assembly, comprises:

a keyboard having a plurality of tongue-activated switches, each switch having an interval of switch activation defined by the depression of the switch;

an encoding means for receiving input from all the tongue-activated switches and, during an interval of switch activation, for generating a waveform which is a function of the specific switch activated; and a magnetic coupling means for receiving the waveform from the encoding means and, during the interval of switch activation, for generating a time-varying magnetic field whose properties are a function of the waveform, whereby upon tongue activation of one of the switches a time-varying magnetic field is created whose properties are uniquely determined by the switch which is activated.

The invention as defined herein includes a keypad having a plurality of switches which identify and invoke differently coded instructions. In this way, the user can effectively operate a motorized wheel chair, a computer or a variety of other devices. The separate keypad switches enable the user through the use of his/her tongue to accurately and easily identify each desired switch. Thus, an unskilled user using the separate keypad switches, even for the first time, can accomplish the desired activity with little or no training.

The addition of magnetic coupling enables the user to use the same battery over an extended period of time. This addition of the magnetic coupling will allow such long battery life even under heavy usage.

Additionally, the transmitter assembly can be encapsulated into the dental appliance and, because of the ultra low power usage, have a shelf life as long as that of the battery.

The addition of the magnetic coupling also allows low power transmission without causing interference with other devices which may be operating in close proximity.

It is an advantage of the present invention to provide a tongue activated communications controller which is easily used by persons having limited physical mobility.

It is an additional advantage of the present invention to provide such a tongue activated communications controller which can be made to operate a broad range of devices.

It is an additional advantage of this invention to provide such a tongue activated communications controller which can be used by large numbers of persons having quadriplegia due to spinal cord injuries and neuromuscular disorders.

It is an additional advantage of this invention to provide a tongue activated communications controller which has an improved battery life, and a shelf life approaching that of the battery itself.

It is yet an additional advantage of this invention to provide a tongue activated communications controller which has decreased size and weight, improved reliability and safety, can be used in numerous applications by disabled and non-disabled persons, and is resistant to interference from adjacent users.

BRIEF DESCRIPTION OF THE DRAWING

For a further understanding of the objects and advantages of the present invention, reference should be made to the following detailed description, taken in conjunction with the accompanying drawing, in which like parts are given like reference numerals and wherein.

DETAILED DESCRIPTION OF THE INVENTION

Figure 1:
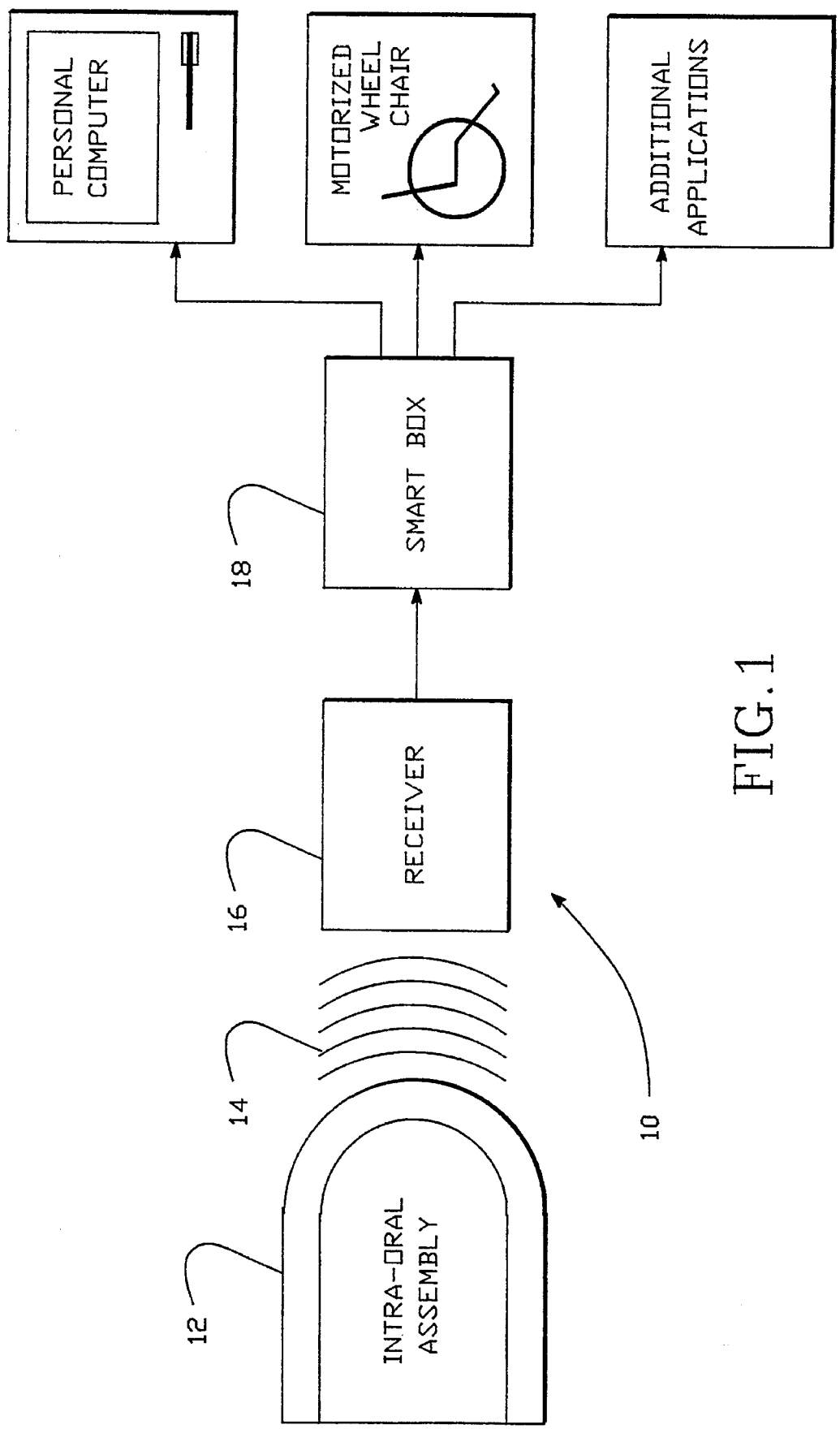
FIG. 1 is a schematic illustration of the tongue activated communications controller in accordance with this invention illustrating usage with a personal computer, a wheelchair as well as additional applications.

Two embodiments of the tongue activated communications controller will be described below. It will be appreciated that many other embodiments are possible within the spirit and scope of this invention. With particular reference to FIG. 1, there is shown the overall schematic of the tongue activated communications controller, in accordance with this invention, generally designated by the numeral 10. The tongue activated communications controller 10 (hereinafter TACC) is illustrated as interfacing with either a personal computer and/or a wheelchair and/or additional applications. The TACC 10 includes an intra-oral transmitter assembly 12. The intra-oral transmitter assembly 12 fits into the mouth of a user and is held in place therein by press fit. It may also be desirable for the intra-oral transmitter assembly 12 to be held in place in a user's mouth by clasps as illustrated in phantom in FIGS. 3 and 4. After installation, the user can transmit encoded signals illustrated by waves 14 to a receiver 16. It is preferable that the transmission be wireless to increase the flexibility of movement of an associated transmitter, however hard-wired embodiments of the TACC are within the scope of this invention. The signals are encoded and are transmitted by the TACC in binary form.

The receiver 16 receives the encoded binary signals and communicates with a smart box 18 which decodes the signals. The smart box 18 comprises a microcomputer; for example, a Z-80 microprocessor or a 4 bit microcontroller would be suitable. The smart box 18 decodes the encoded binary signal and determines which switch on the keyboard has been depressed. The smart box 18 sends a control signal to the desired device for carrying out the appropriate action, such as inputting to a personal computer or directing the motion of a wheelchair. The smart box 18 includes the software for monitoring the received signal and converting it to the appropriate control signal as will be more fully appreciated hereinafter.

Figure 2:
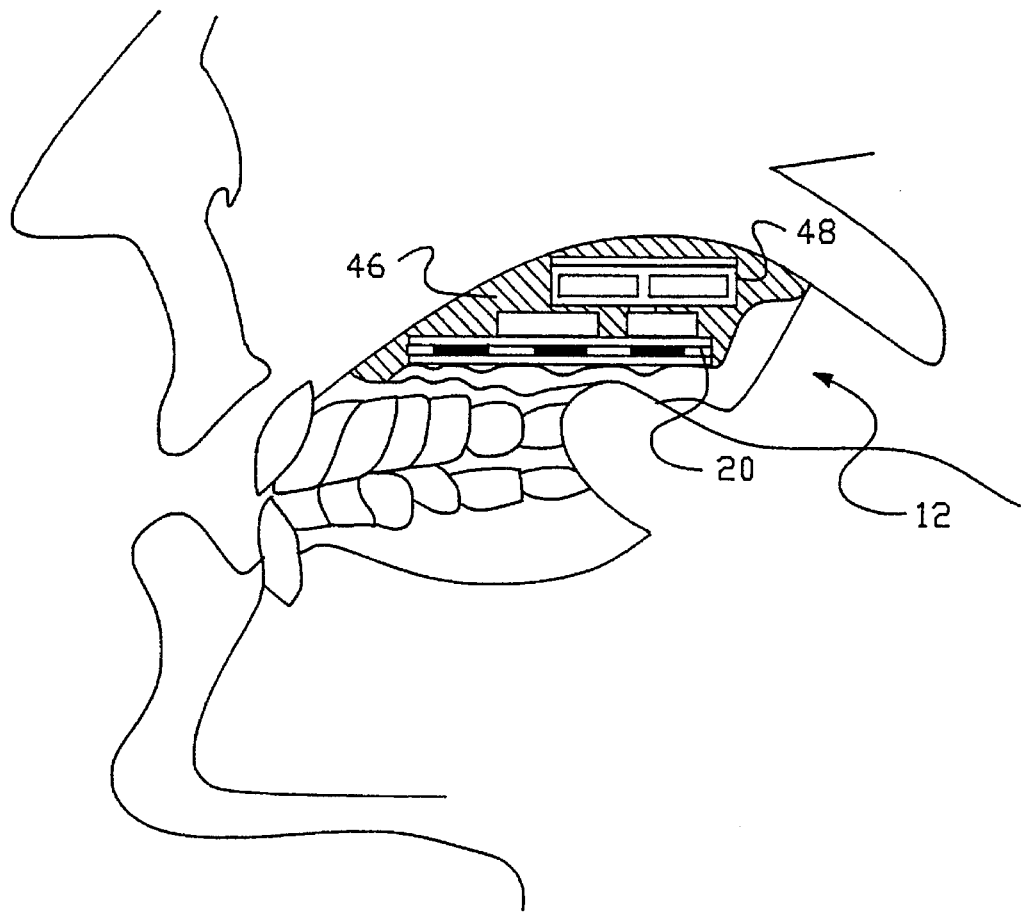
FIG. 2 is a partial sectional schematic view of the tongue activated communications controller in accordance with this invention installed in the mouth of the user.
Figure 3:
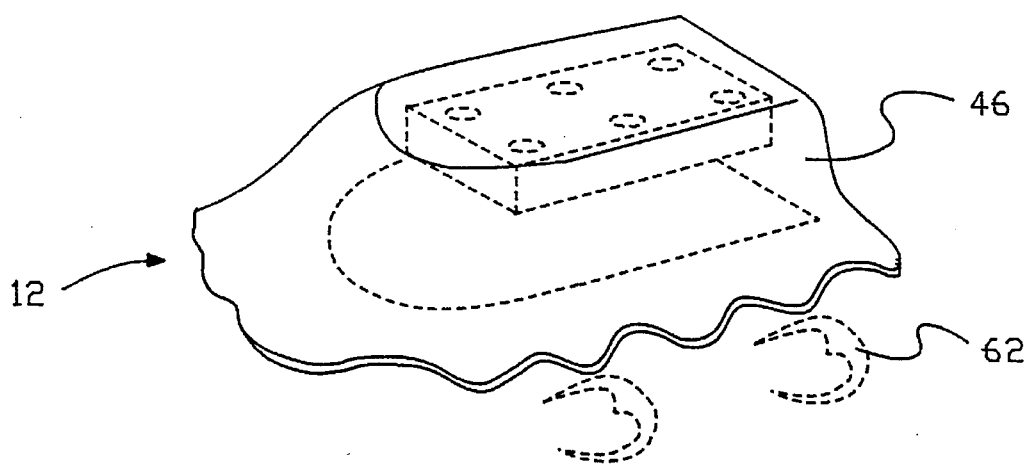
FIG. 3 is a perspective view of the assembled tongue activated communications controller.
Figure 4:
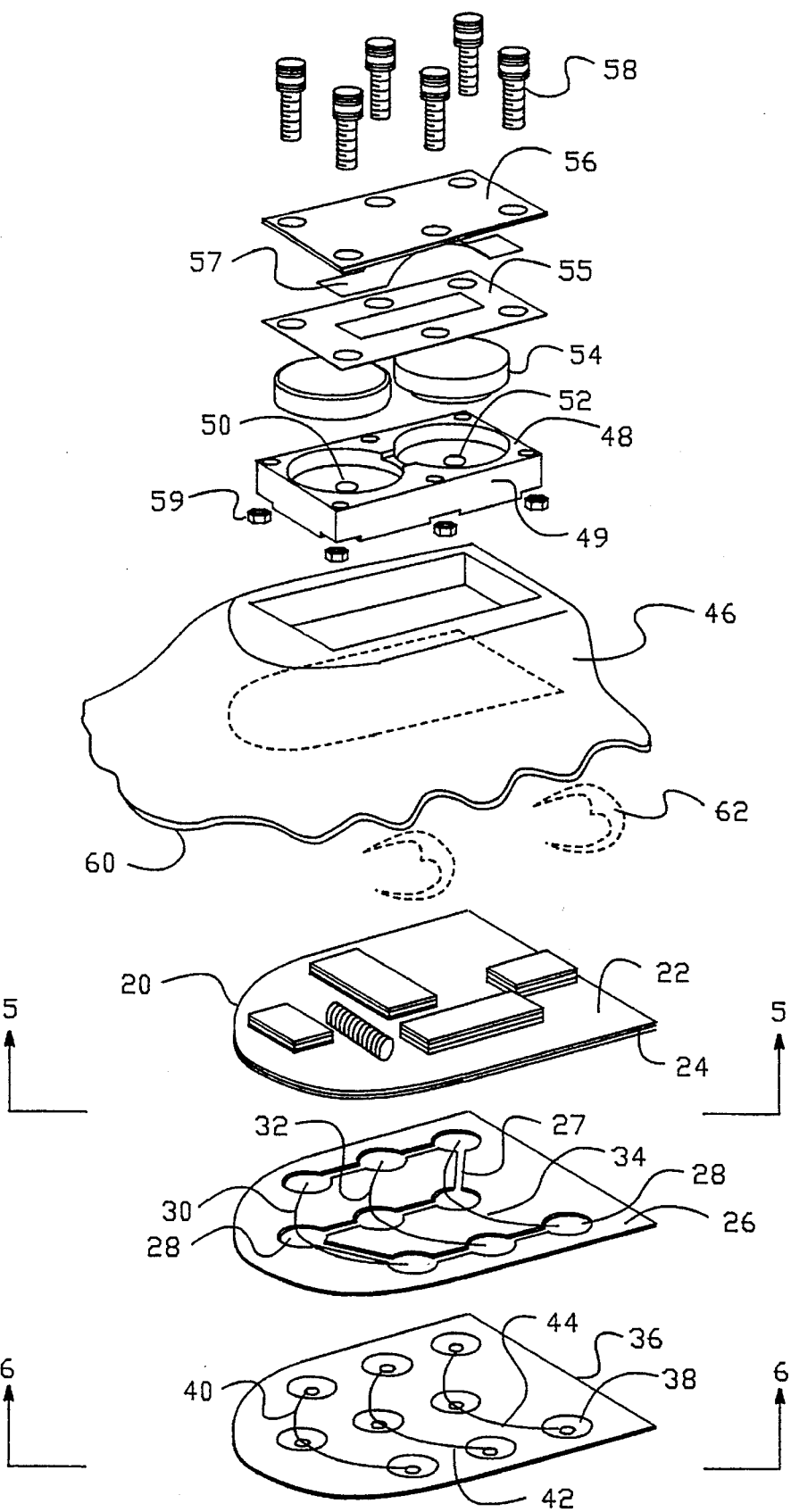
FIG. 4 is an exploded perspective view of the tongue activated communications controller of FIG. 3.

With particular reference to FIGS. 2–4, there is shown the details of the intra-oral transmitter assembly 12. The intra-oral transmitter assembly 12 includes a PC board 20. The PC board 20 is a two-sided board having a first side 22 with transmitter electronics and a second side 24 with the electrical circuit for the keyboard. Thus, the PC board in accordance with this invention includes both the transmitter electronics and circuitry for switching from one keyboard position to another.

The first side 22 includes an encoder 96, a transmitter 98, a timer 100, an oscillator 102 and a voltage regulator 104. A detailed description of the above elements is set forth below with reference to FIG. 8. The particular electrical devices are preferably low power, high speed semiconductors and are preferably a combination of CMOS integrated circuits and discrete devices. These types of semiconductor devices are preferred because they are compatible with the speed of the 2 MHz crystal oscillator 102.

The intra-oral transmitter assembly further includes an adhesive spacer 26 having a plurality of openings 28 and a keyboard membrane 36 including a plurality of conductive key pad members 38. The keyboard membrane 36 is bonded to the PC board 20 using the adhesive spacer 26. The adhesive spacer 26 is an acrylic adhesive which creates a water tight seal between the keyboard membrane 36 and the PC board 20. The adhesive spacer 26 has channels 27 to permit the movement of air trapped within the channels 27 and the openings 28 as one of the conductive key pad members 38 is depressed by the user's tongue.

The adhesive spacer 26 spaces the membrane 36 away from the second side 24 to prevent short circuiting of the keyboard. Therefore, the adhesive is made from an insulating material, such as an acrylic based adhesive. Additionally, the adhesive spacer 26 acts as a moisture barrier to prevent corrosion and disfunctioning of the electrical circuits. This is especially important since much of the life of the intra-oral transmitter assembly 12 is spent in a moist or wet environment.

In the preferred embodiment, there are three rows of openings 28. The rows have an arc shaped design, designated by the lines having reference numerals 30, 32 and 34 for each of the first, second and third rows, respectively. The arc shaped design accommodates the conductive key pad members 38. The conductive key pad members 38 are similarly divided into three rows 40, 42 and 44, designating the first, second and third rows respectively. As will be appreciated from the more detailed explanation found with reference to FIG. 6, the conductive key pad members 38 are generally flat and each includes a nipple 92 which protrudes away from the second side of the PC board. Pressure from the tip of a user's tongue deforms the pad members 38 and pushes the conductive surface of the pad members 38 through the opening 28 of the adhesive spacer 26 and into electrical contact with the second side 24 of the PC board as best shown in FIG. 7.

The intra-oral transmitter assembly 12 is encapsulated by an encapsulant 46 made of methyl methacrylate. As shown more clearly in FIGS. 2 and 3, the methyl methacrylate encapsulates the PC board 20 the adhesive spacer 26 and the keyboard membrane 36. The bottom of the operating surface of the keyboard membrane 36 which includes the nipples 92 is exposed for access by the user's tongue and not encapsulated.

The encapsulant 46 has a recess defining a battery compartment 48. Within the compartment 48 are two electrically conductive pads 50 and 52 which are electrically connected to the voltage regulator. A pair of batteries 54 are placed in electrical contact with the pads 50 and 52. In order to protect the user the batteries 54 are sealed in the battery compartment 48 by a gasket 55 and a cover 56. The cover 56 is placed over the batteries 54 for securing the batteries 54 into electrical contact with the pads 50 and 52. The cover 56 includes an electrical contact 57 for bridging the two batteries. The cover 56 is secured to the battery compartment 48 by use of screws 58 and nuts 59 in the battery compartment.

The cover 56 is made from fiberglass and is mounted almost flush with the encapsulant 46. In the preferred embodiment, the encapsulant encapsulates the cover 56. This ensures a comfortable fit of the intra-oral transmitter assembly 12 to the roof of the mouth of the user.

The battery compartment 48 has walls 49 made of A-Butyl Styrene. This provides a double insulation in combination with the encapsulant to limit any passage of fluids or gases between the inside of the battery compartment 48 and the user's mouth.

The encapsulant further has teeth interface members 60 which comprise the shaped outside edges of the encapsulant 46. The edges are shaped in the form of the profile of the inside of the teeth and gums in the mouth of the user. In order to accomplish this, the encapsulant 46 is cast into an impression of the user's mouth, using standard dental techniques. This allows the intra-oral transmitter assembly 12 to be press fit to conform to teeth and gum and the roof of the mouth of the user. Additionally, this procedure ensures that the fit of the intra-oral transmitter assembly 12 will be comfortable and secure within the user's mouth.

In some mouths, additional security is desirable. As shown in phantom in FIGS. 3 & 4, a clasp 62 can be embedded in the encapsulant 46 and secured to the teeth using standard dental techniques.

Figure 5:
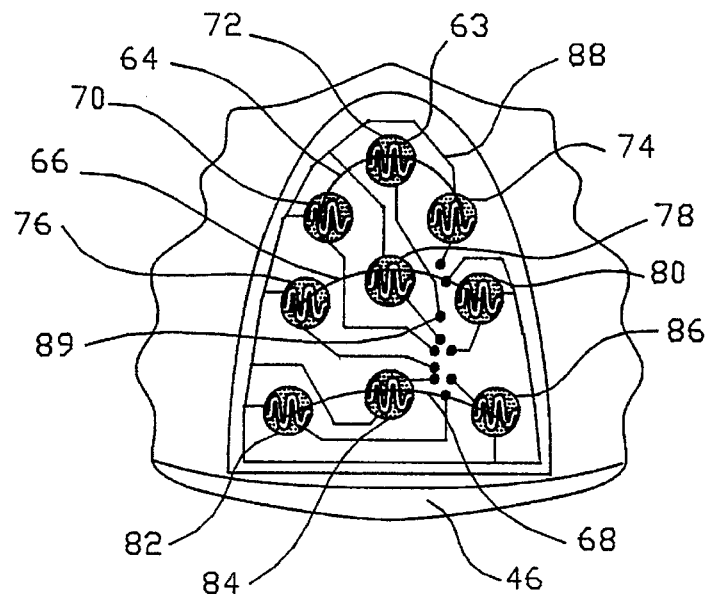
FIG. 5 is an enlarged bottom view of the assembled tongue activated communications controller illustrating the electrical circuit of the keypad.

With particular reference to FIG. 5, there is shown the second side 24 of the PC board 20 having the electrical circuit for the keyboard. The circuitry is divided into three arc shaped rows 64, 66 and 68. The arc shaped rows 64, 66 and 68 are compatible with the earlier described first, second and third rows, 30, 32 and 34, respectively, of the adhesive spacer 26 and the first, second and third rows, 30, 32 and 34, respectively, of the keyboard membrane 36. Thus, the conductive key pad members 38 of the keyboard membrane 36 align with the openings 28 of the adhesive spacer 26 which are aligned with the switches 63.

Each switch 63 is approximately 0.175 inch in diameter. The switches 63 are divided into three rows. The first row comprises switches 70, 72 and 74, which are consecutively numbered switches 1, 2 and 3. The second row comprises switches 76, 78 and 80, which are numbered switches 4, 5 and 6. The third row comprises numbered switches 82, 84 and 86 which are switches 7, 8 and 9, respectively.

Each of the switches 63 is generally round in shape. The center-to-center spacing of adjacent switches is approximately equal and is approximately 0.3 inch. This is true except for the center-to-center spacing of switch 2 to switch 4, which is somewhat larger, approximately 0.37 inch.

As can be seen from FIG. 5, each of the switches 63 is electrically connected by conductive lines 88 and holes 89 in the PC board 20 to the first side 22 of the PC board 20. Thus, when an electrical connection is made across the switch 63, a signal for that switch is sent to the first side 22 keyboard electronics and transmitted by the intra-oral transmitter assembly 12 to the receiver 16.

Figure 6:
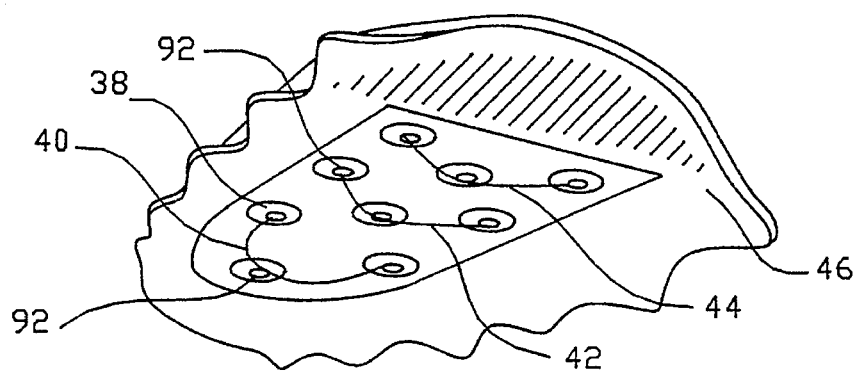
FIG. 6 is an enlarged bottom view of the tongue activated communications controller of FIG. 3.
Figure 7:
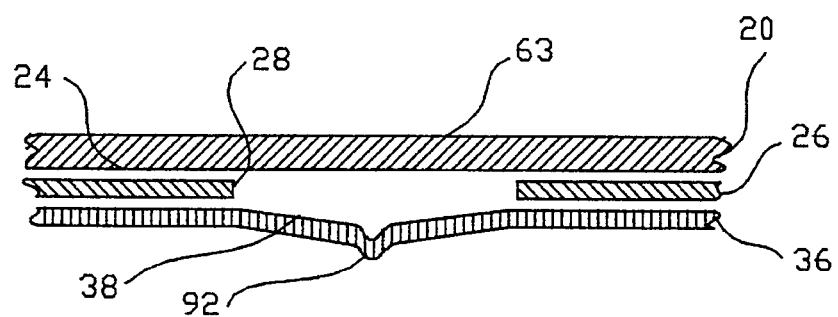
FIG. 7 is an enlarged cross-sectional view of the keyboard in accordance with this invention.

With particular reference to FIG. 6, there is shown the bottom side of the keyboard membrane 36. The keyboard membrane 36 is made from mylar and has conductive ink applied to it to create pad members 38. The conductive ink provides a conductive path across one of the switches 63 when one of the corresponding pad members 38 is depressed. The adhesive spacer 26 spaces the keyboard membrane 36 away from the PC board 20 sufficiently (approximately 0.002 inch) so that no electrical contact is made until one of the pad members 38 is depressed. The channels 27 facilitate the depression of the pad members 38 by allowing the displacement of air between the pad members 38 and the PC board 20.

As shown most clearly in FIG. 7, each of the pad members 38 have a nipple 92. The nipple 92 is in the form of a Braille raised dot as to both diameter and shape made with a Braille slate stylus. This provides the user with accurate tactile feedback.

Similar to the switches 63, the pad members 38 are 0.175 inch in diameter. Adjacent pad members 38 are spaced apart 0.3 inch, center-to-center. The distance between the middle pad in the first row 40 and the middle pad in the second row 42, which corresponds to switches 2 and 4 are somewhat larger than the 0.3 inch center to center spacing and match exactly the spacing of switches 2 and 4. The nipples 92 are formed so as to facilitate the detection of one of the pad members 38 with the tongue. Approximately 0.50 ounce of force is required to depress one of the pad members 38 to make electrical contact such that a circuit for switch 63 is completed.

Figure 8:
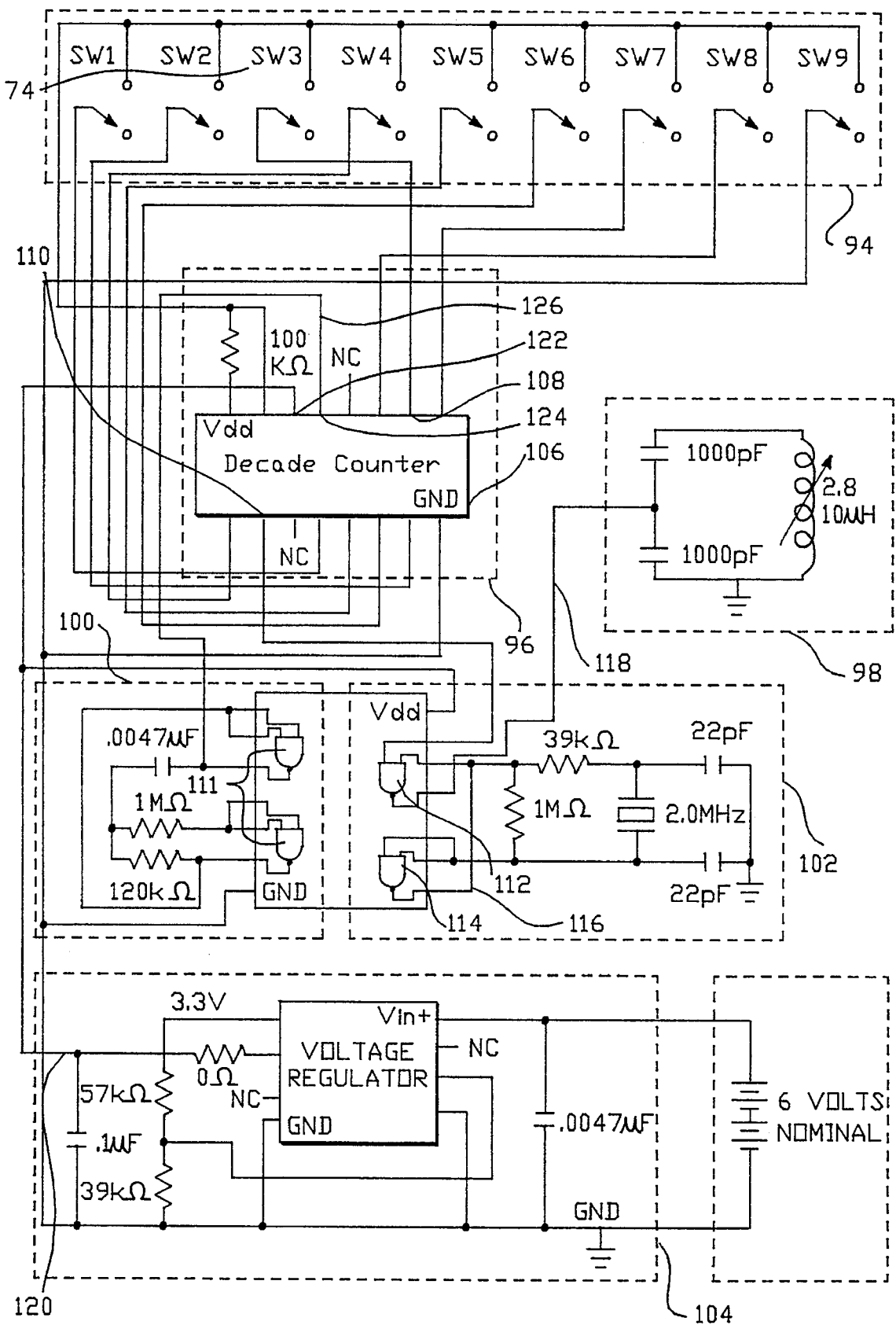
FIG. 8 is an electrical circuit schematic of the tongue activated communications controller in accordance with this invention.

With respect to FIG. 8, there is shown the electrical circuit schematic for the intra-oral transmitter assembly 12. As shown, the assembly 12 includes a keypad 94, an encoder 96, a transmitter 98, a timer 100, an oscillator 102 and a voltage regulator 104. The oscillator 102 preferably oscillates at a fixed frequency of 2 MHz.

The keypad 94 comprises the second side 24 switches 1 through 9 as shown in the FIG. 8. When one of the switches 63 is closed, an electrical signal is sent to the encoder 96. The signal received is encoded using a decade counter 106; for example, if switch 3, designated by the numeral 74, is closed, an electrical signal is received at Q4 of the decade counter designated by the numeral 108. This is also pin position 10 of the decade counter 106. The signal is encoded and sent to an output of the decade counter designated by Q1 and the reference numeral 110. This is also known as pin position 2 of the decade counter.

The encoded output of the decade counter, Q-1, 110, is sent to the first NAND gate 112 of the oscillator 102. The encoded signal sent to the first NAND gate 112 is mixed with a carrier signal created by the oscillator 102.

The oscillator 102 uses a second NAND gate 114, a crystal and appropriate discrete components to generate a 2 MHz carrier signal. The carrier signal is then sent through conductive line 116. The carrier signal is then mixed with the encoded signal at the first NAND gate 112. The output of the mixed signal is sent to the transmitter 98 over conductive line 118.

The transmitter 98 transmits at 2 MHz frequency using the carrier signal created by the oscillator 102. In the embodiment of the transmitter 98 shown in FIG. 8, the transmitter 98 has a variable inductance and can be adjusted to tune the resonant frequency of the transmitter 98 to the carrier signal of 2 MHz.

The receiver 16 detects the encoded signal from the intra-oral transmitter assembly 12 and filters out the carrier signal. The encoded modulated signal, which remains, is passed to the smart box 18 and decoded to determine which switch on the keyboard has been depressed. The smart box 18 translates the encoded modulated signal into a control signal for controlling and operating various devices, as shown in FIG. 1. The control signal may be analog or digital in nature. The operation of the receiver 16 and smart box 18 will be more fully appreciated with reference to FIGS. 11–13.

The frequencies of the various modulating signals transmitted by the intra-oral transmitter assembly 12 are determined by the timer 100. The voltage regulator 104 reduces the battery voltage potential of nominally 6 V to a potential of 3.3 V. This provides the power to the semiconductor devices, the decade counter 106 and NAND gates 111. The 3.3 V potential also represents the binary high for the digital logic. The 3.3 V potential is sent over conductive line 120 to the decade counter enable 122 of the decade counter 106. This is also known as pin position 14 of the decade counter 106.

Thus, when the voltage regulator 104 provides the 3.3 V signal, the decade counter 106 is enabled and the clock input 124 is tied to the timer 100. As can be seen, the clock input 124 is tied to the output of the timer 100 by conductive line 126 and the voltage regulator output is tied to the decade counter enable 122 by conductive line 120. Thus, when the clock is enabled, an encoding signal corresponding to one of the switches 63, namely the switch depressed, is sent from the decade counter 106 to the oscillator 102 and then transmitted.

Figure 9:
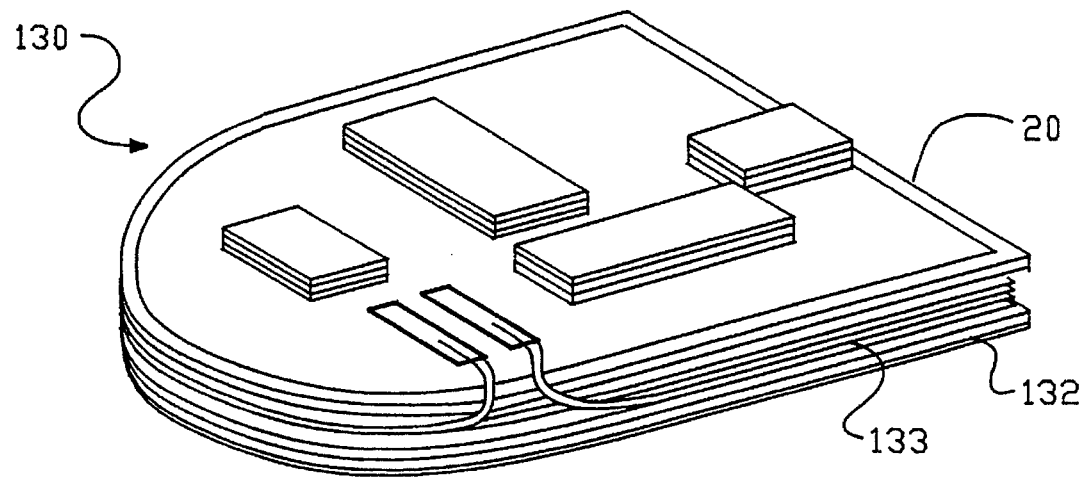
FIG. 9 is a side perspective view of a second embodiment of the tongue activated communications controller in schematic illustrating a fixed inductor wrapped around the perimeter of a PC board.

With particular reference to FIG. 9, there is shown a second embodiment of the intra-oral transmitter assembly generally denoted by the numeral 130. In the second embodiment, there is a groove 132 having a depth within the range of 0.25 inch to 0.10 inch around the perimeter of the PC board 20. The wire is wound around the PC board replacing the variable inductance surface mounted component of the earlier described embodiment. Magnet wire 133 of 39 gage is tightly wound around groove 132 and is held in place thereby. Wrapping the magnet wire 133 creates an inductor having a fixed value, in the preferred embodiment, the value ranges between 2.8 µH and 10 µH. Unlike the first embodiment the inductance can not be varied after assembly. However, the inductance can be measured on a case by case basis. The magnet wire 133 is connected to the first side 22 of the PC board in the same location where the variable inductor was found in the first embodiment 12.

Figure 10:
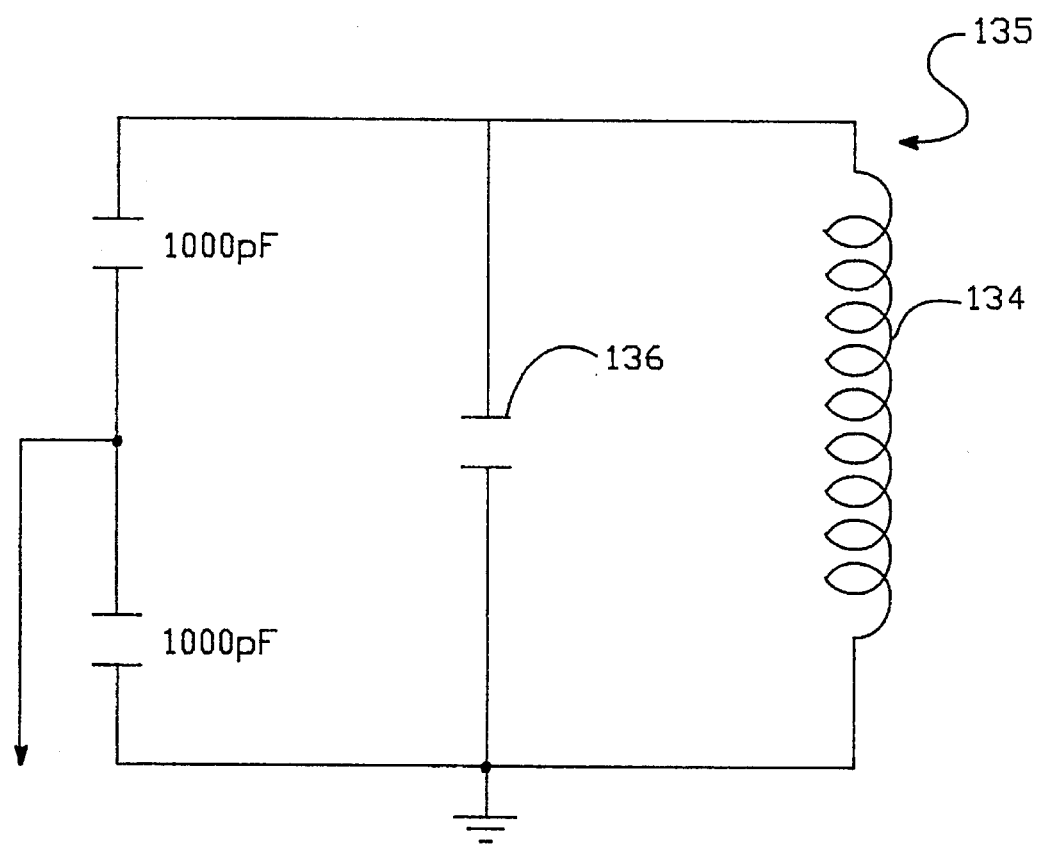
FIG. 10 is an electrical circuit schematic of a second embodiment of the transmitter circuit of the tongue activated communications controller in accordance with this invention.
Figure 11A:
FIG. 11 is a timing diagram illustrating encoded transmission from the tongue activated communications controller in accordance with this invention.
Figure 11B:
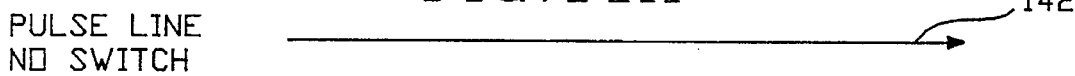
Figure 11C:
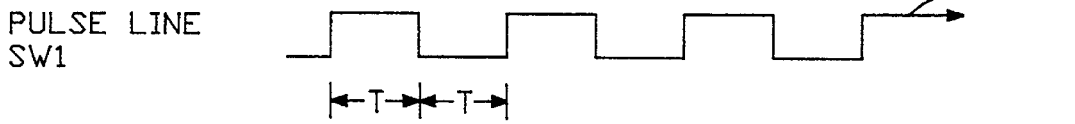
Figure 11D:
Figure 11E:
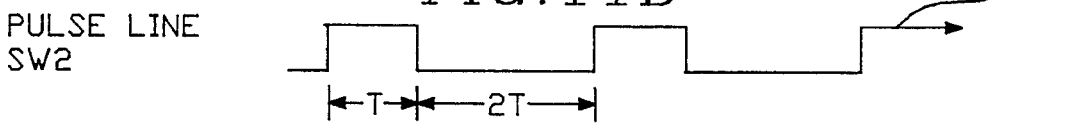
Figure 11F:
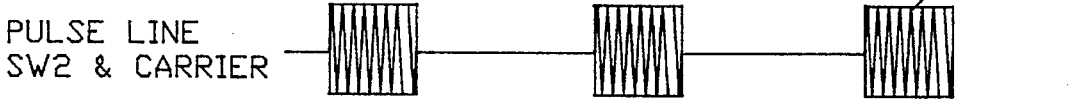
Figure 11G:
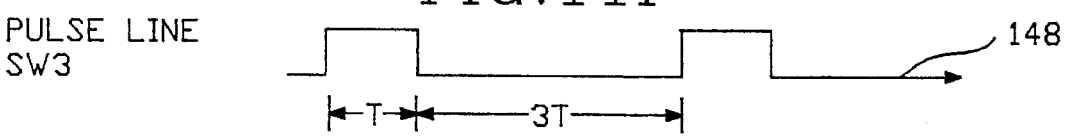

As can be appreciated, a new transmitter circuit, generally designated by the numeral 135, is necessary to accommodate the second embodiment of the intra-oral transmitter assembly 130. The corresponding circuit diagram is shown in detail in FIG. 10. The transmitter assembly 130 includes a fixed inductor 134 which comprises the magnetic wire 133 wound around the PC board groove 132, as described earlier. The inductor 134 is a fixed value that ranges between 2.8 µH and 10 µH. The transmitter assembly 130 further includes a pair of 1000 Pf capacitors and a tuning capacitor 136. The tuning capacitor 136 is inserted into the circuit to assure that the tuned resonant frequency of the transmitter matches the 2 MHz carrier. The value of the tuning capacitor 136 is selected accordingly. This ensures the signal is accurately received by the receiver 16.

When the signal is transmitted, it is done so by a wireless transmission. If it was desirable for there to be a hard wire between the intra-oral transmission assembly 12 and the smart box 18, the signal would be tapped directly from the output of the decade counter 106. In this embodiment no transmitter or oscillator would be necessary.

FIG. 11 illustrates the encoding of the signal transmitted by either of the intra-oral transmitter assemblies 12 or 130. The timer sends out a clock signal represented by pulse line 140. When none of the switches 63 has been activated, no signal is sent out from the decade counter 106. This is schematically represented by a straight pulse line 142. When one of the switches 63 is depressed a unique pulse line is generated. For example, when switch 1 has been depressed, a pulse line 144 is created. Pulse line 144 is a square wave line having a period of 2 T, where T is one timer period. This form of modulation is called pulse coded modulation.

Coded pulse line 144 is then combined with the 2 MHz carrier and forms pulse line 145. Pulse line 145 is then transmitted to the receiver 16 where the carrier is filtered out and the signal decoded.

When switch 2 is depressed, a pulse line 146 having a period of 3 T (1 T high and 2 T low) is created. Pulse line 146 is combined with the 2 MHz carrier to form pulse line 147 and is then transmitted to receiver 16. Similarly, when switch 3 is depressed a 4 T (1 T high and 3 T low) pulse line 148 is created. Again, it is combined with the carrier and transmitted. The remaining switches 63 follow the same pattern.

Figure 12:
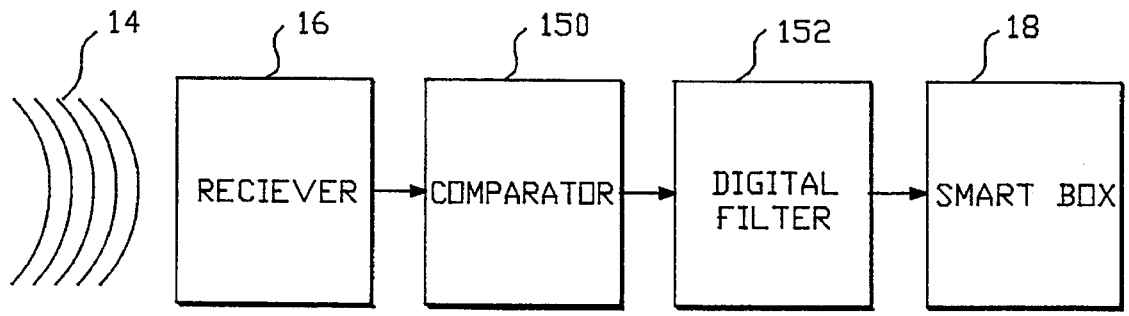
FIG. 12 is a schematic illustration of the encoded signal being received by the tongue activated communications controller in accordance with this invention.

FIG. 12 illustrates receipt of the wireless transmission of the signal from either of intra-oral transmitter assemblies 12 or 130. As described above, the receiver filters out the carrier portion of the signal. The receiver 16 is a modified AM receiver which has been tuned to the carrier frequency of 2 MHz. This is done by adjusting the core and changing the capacitors to stabilize the reception by minimizing drift. The receiver 16 uses an amplitude modulation detection scheme to recover the encoded signal.

The receiver 16 sends the demodulated, encoded signal to a comparator 150 which converts the wave form into binary format. The comparator 150 sends the signal to a digital filter 152 which converts the encoded signal into a square wave. The digital filter 152 sends the resulting, filtered signal to the smart box 18.

The smart box 18 comprises a standard microcomputer architecture. The preferred embodiment of the smart box includes a single board computer which has a plurality of input and output ports, e.g. Prolog, STD-7000 System 7806 Z-80A Multifunction CPU card 7904 TTL Decoded I/O Utility Card. The smart box 18, using the software described in detail below, generates a control signal for controlling and operating various devices. The control signal may be digital or analog or a modified digital signal. The control signal may be altered as needed using the smart box and the system software.

In order to generate the correct signal, the smart box 18 uses the system software to determine which switch has been depressed and activates its own corresponding switch to direct the desired device to perform the desired function.

Figure 13:
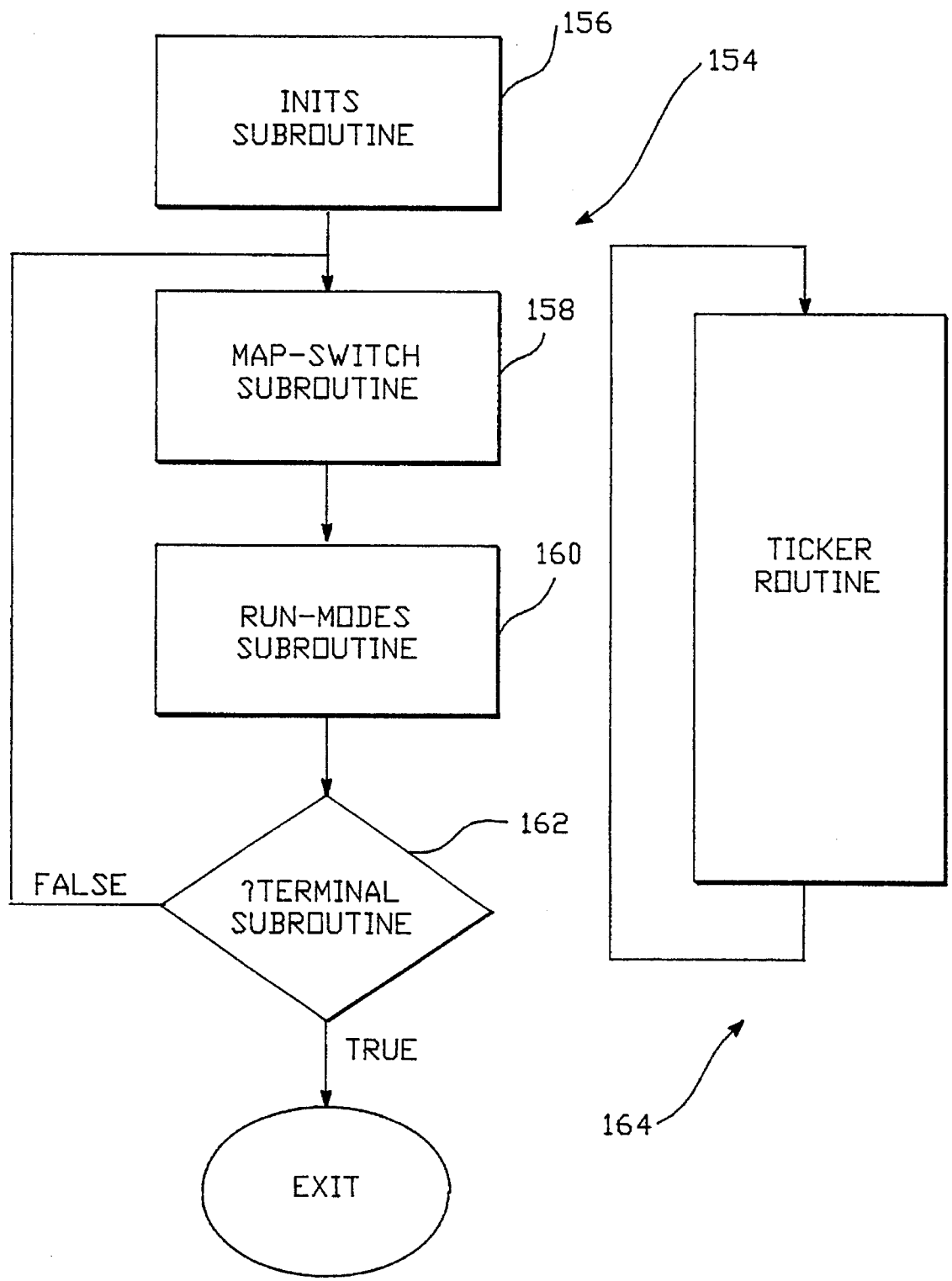
FIG. 13 is a flow chart of the software enclosed in the smart box in accordance with this invention.

The system software referenced above will now be described with reference to FIG. 13. At the top level of the software, there are two software loops operating at all times. The main routine is called TOP, generally designated by the numeral 154. TOP performs initial and preparatory routines and then enters into a repeating loop. Within this repeating loop the computer executes the MAP-SWITCH 158 subroutine which selects the mapping of the switch position identification for different keyboard layouts. Upon completion of MAP-SWITCH 158, TOP 154 enters another subroutine called RUN-MODES 160. After executing RUN-MODES 160, the software checks for keyboard inputs in another subroutine called ?TERMINAL 162. If a key is activated on a programmer's computer, the Main Event loop within TOP 154 ends. This programmer's computer is connected to the smart box 18 only during programming and testing. Otherwise, the Main Event loop repeats, continuing with the MAP-SWITCH subroutine. The Main Event loop is comprised of MAP-SWITCH 158, RUN-MODES 160 and ?TERMINAL 162. The TOP 154 routine remains within the RUN MODES 160 as long as one of the pad members 38 is depressed to cause activation of one of the switches 63.

At regular 0.512 msec intervals, the computer halts whatever it is doing in the TOP routine and executes another routine called TICKER, generally designated by the numeral 164. TICKER 164 is the interrupt service routine which reads the binary signal from the receiver 16 and updates the clock variables to reflect the time between each low to high transition edge of the pulse line as described with reference to FIG. 11. The TICKER 164 routine prepares data to be sent out to those devices which require repeating outputs, for example, a Macintosh computer mouse port. In other cases, routines within RUN-MODES 160 send out control information directly without using TICKER 164, for example wheelchair controllers. The TICKER 164 routine calculates the length of time between successive low to high transition edges and stores information in the software variables NEW-CLOCK and OLD-CLOCK. These variables are read into RUN-MODES 160 to determine which of the switches 63 has been closed.

There are several software subroutines within the smart box 18. As shown in FIG. 13, there is an initialization subroutine called INITS, designated by the reference numeral 156, which performs the functions of initializing variables and configuring the timers in the smart box 18 necessary for the interrupt service routine. INITS 156 also performs a one time initialization of variables handled regularly within the interrupt service routine, TICKER 164 and establishes the location of TICKER 164 in memory. The TICKER 164 routine runs whenever its interrupt is encountered and handles all timing calculations.

Additionally, INITS 156 performs the functions of preparing the variables used in identifying each switch 63, configuring the variables that control the acceleration behavior of a device such as a computer mouse and configuring the motorized wheelchair controller so that the wheelchair is stationary upon initial operation.

The MAP-SWITCH 158 contains a simple one to one table which changes the logical identity associated with each switch so that the switches 1 through 9 can be mapped anywhere on the keypad.

The RUN-MODES 160 selects one of the available operation modes which the smart box 18 operates. For example, the modes in the smart box 18 are ?TEST, MOUSE or CHAIR. ?TEST configures the operation of the intra-oral transmitter assembly 12 into a test mode; MOUSE converts operation of the intra-oral keypad into a Macintosh mouse emulation; and CHAIR converts the operation of the intra-oral keypad into the directional control of a powered wheelchair. Other additional operational modes can be added as required and then the smart box will behave in one of these modes as desired.

In the CHAIR mode, the user depresses one of the conductive key pad members 38 to control a motorized wheelchair. In a preferred embodiment a DUFCO controller is used and the CHAIR subroutine produces the output necessary to operate such a controller. The user can move one of 8 directions; forward, forward right, right, . . . or send a stop signal.

The CHAIR mode includes a lower level subroutine entitled, TACC-KEY? which examines the switch closure data from either one of the transmitter assemblies 12 or 130 to determine which switch if any, has been closed. There are several error suppression algorithms within the TACC-KEY? subroutine to minimize the effect of key bounce and transmission signal degradation.

The CHAIR mode includes another lower level subroutine entitled, RUN-CHAIR, which reads which switch the user has closed and performs a table look-up to determine which bits (binary values) to set high or low in the output signal. This output signal is composed of a four bit word: a forward bit, a reverse bit, a left bit and finally a right bit. These bits determine the direction that the wheelchair moves. All acceleration and velocity ramping is handled by the DUFCO wheelchair controller hardware. These bits form a command instruction for the wheelchair controller and when outputted, the wheelchair controller responds with movement.

An additional low level CHAIR subroutine is entitled, STOP-CHAIR which sets the four bit signal sent to the DUFCO wheelchair controller to zero. This instructs the wheelchair to stop.

The mouse mode includes low level routines which translate switch closure into Macintosh mouse emulation. The algorithm for performing this emulation is set forth in Appendix A, which represents the source code for the above software, is attached hereto and made part hereof.

Another embodiment of the tongue activated communications controller 10 uses a magnetic field for transmissions. The TACC 10 shown in block diagram form in FIG. 17 includes an intra-oral transmitting assembly 12 having nine tongue activatable switches 63, a battery 54, an encoder 96 for generating a signal which identifies the activated switch and reports the status of the battery 54 voltage level and a transmitter circuit 98 for generating a radio frequency (RF) magnetic field corresponding to the resulting encoder signal.

The tongue activated communications controller 10 also includes a receiver 16 (FIG. 14) responsive to the magnetic field generated by the intra-oral transmitting assembly 12; and a smart box 18 for decoding the received signal, displaying system status to the user (see for example, FIG. 15) and generating and monitoring appropriate signals and signalling sequences for control and monitoring of such things as a motorized wheelchair, bed, lights, environmental controls, computer, TV, VCR and numerous other devices.

Figure 14:
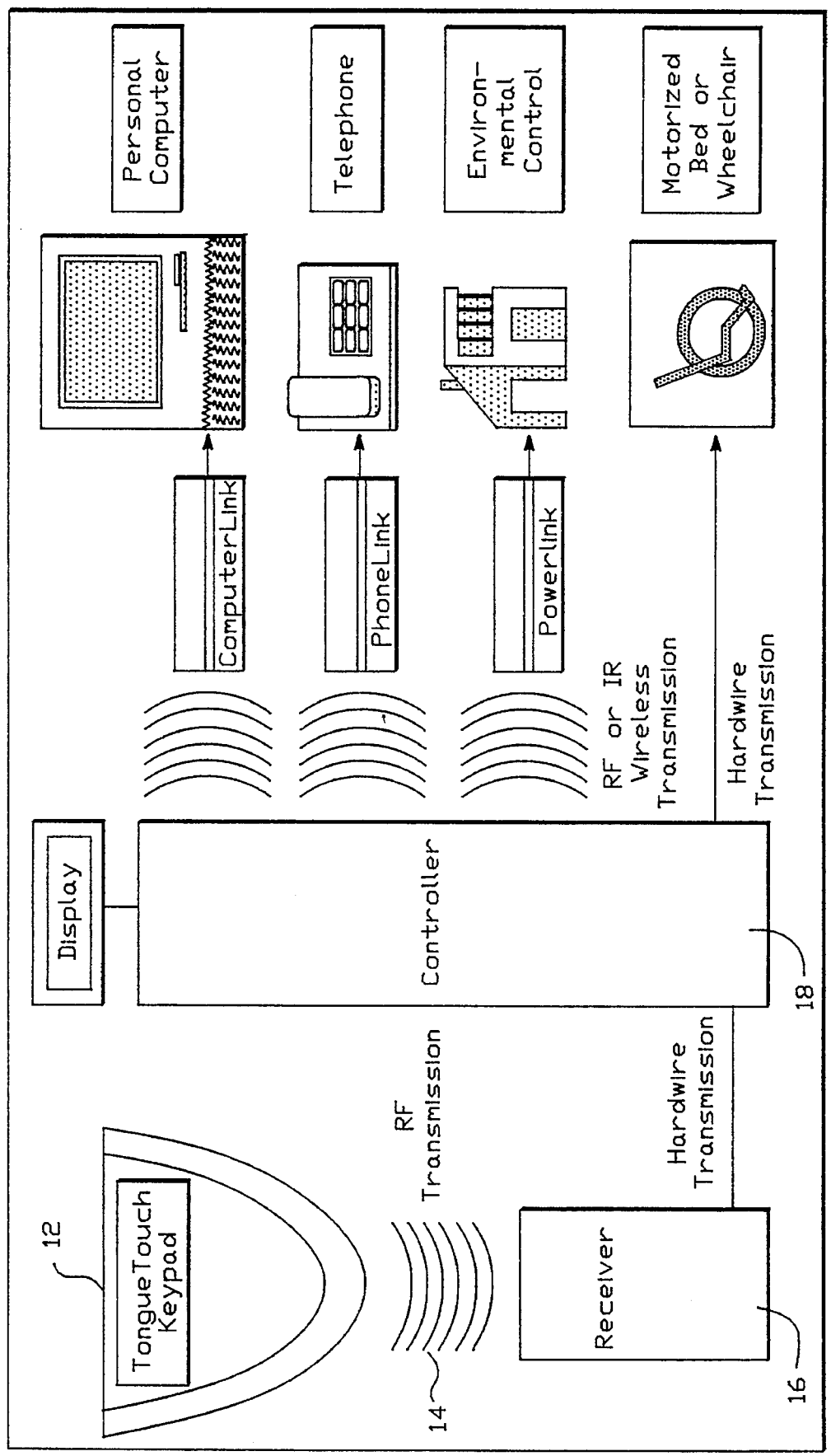
FIG. 14 is a schematic illustration of an alternate tongue activated communications controller for transmission by means of a magnetic field.
Figure 15:
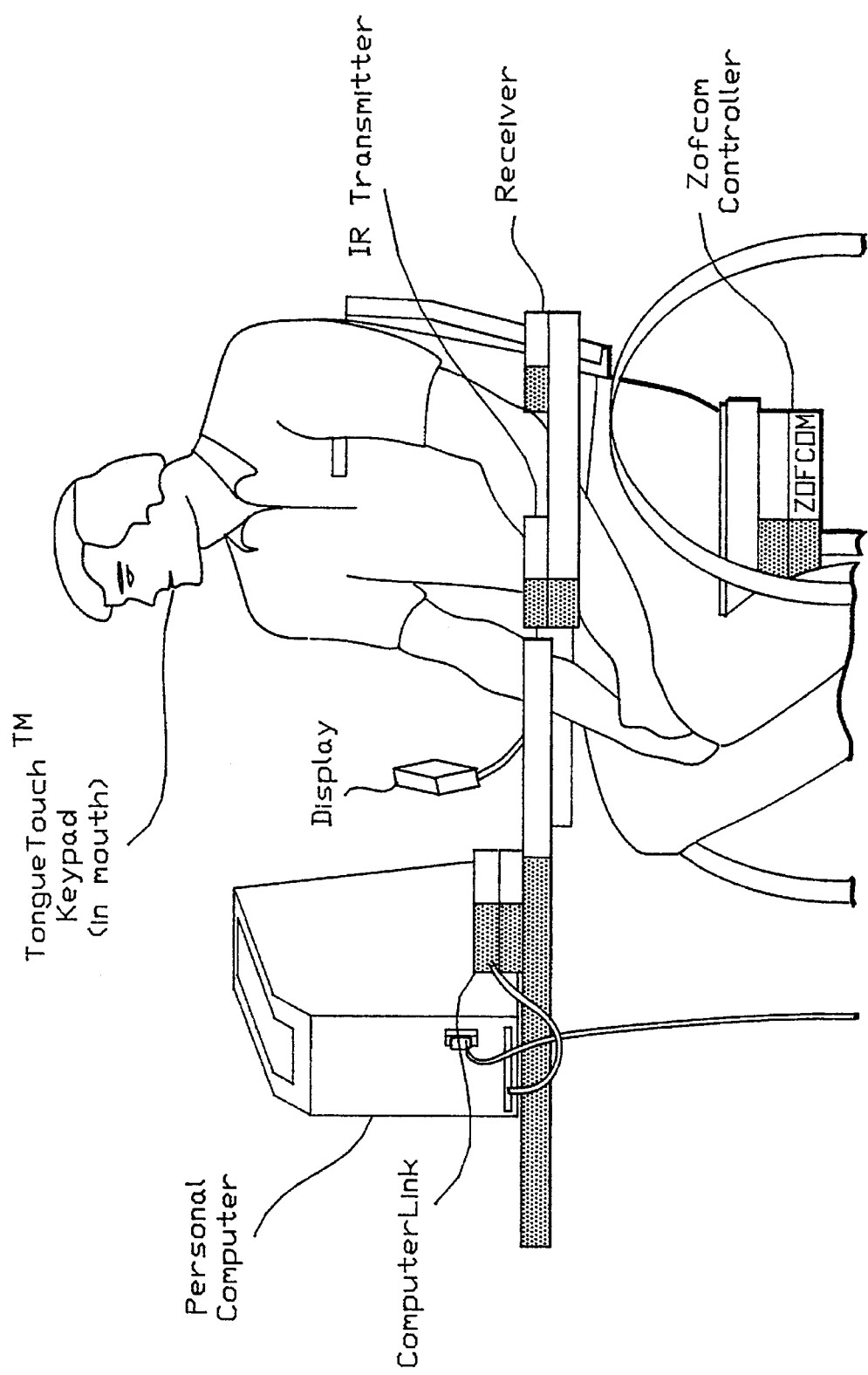
FIG. 15 is a pictorial diagram showing a typical installation of the tongue activated communications controller for transmission by means of a magnetic field.
Figure 16:
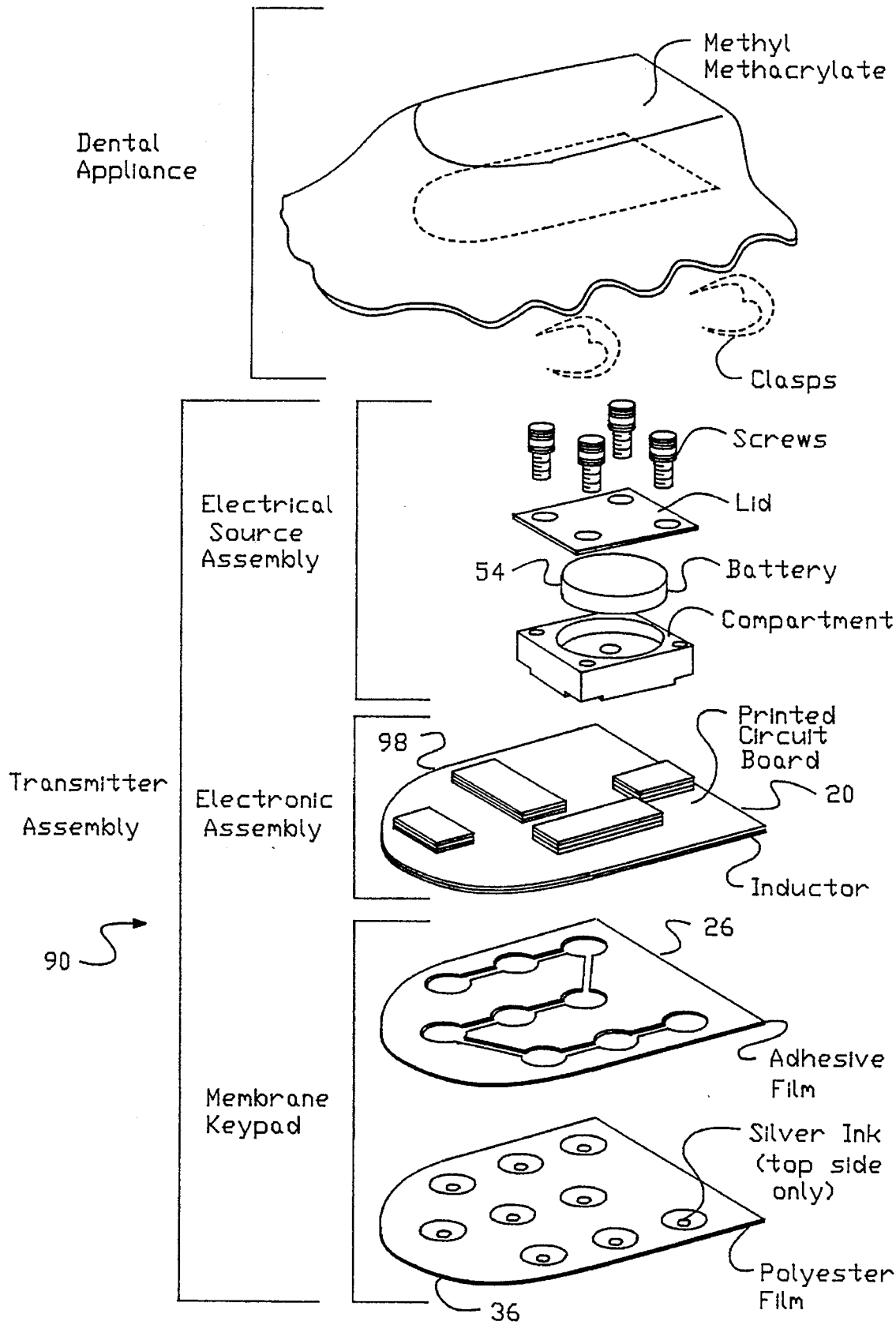
FIG. 16 is an exploded perspective view of the intra-oral transmitting assembly for transmission by means of a magnetic field.

FIG. 14 also shows communication between the smart box 18 and various device "links" by means of both radio frequency (RF) link or infrared (IR) link. An typical application of an IR link between the smart box 18 and a desktop computer is depicted in FIG. 15.

Figure 17:
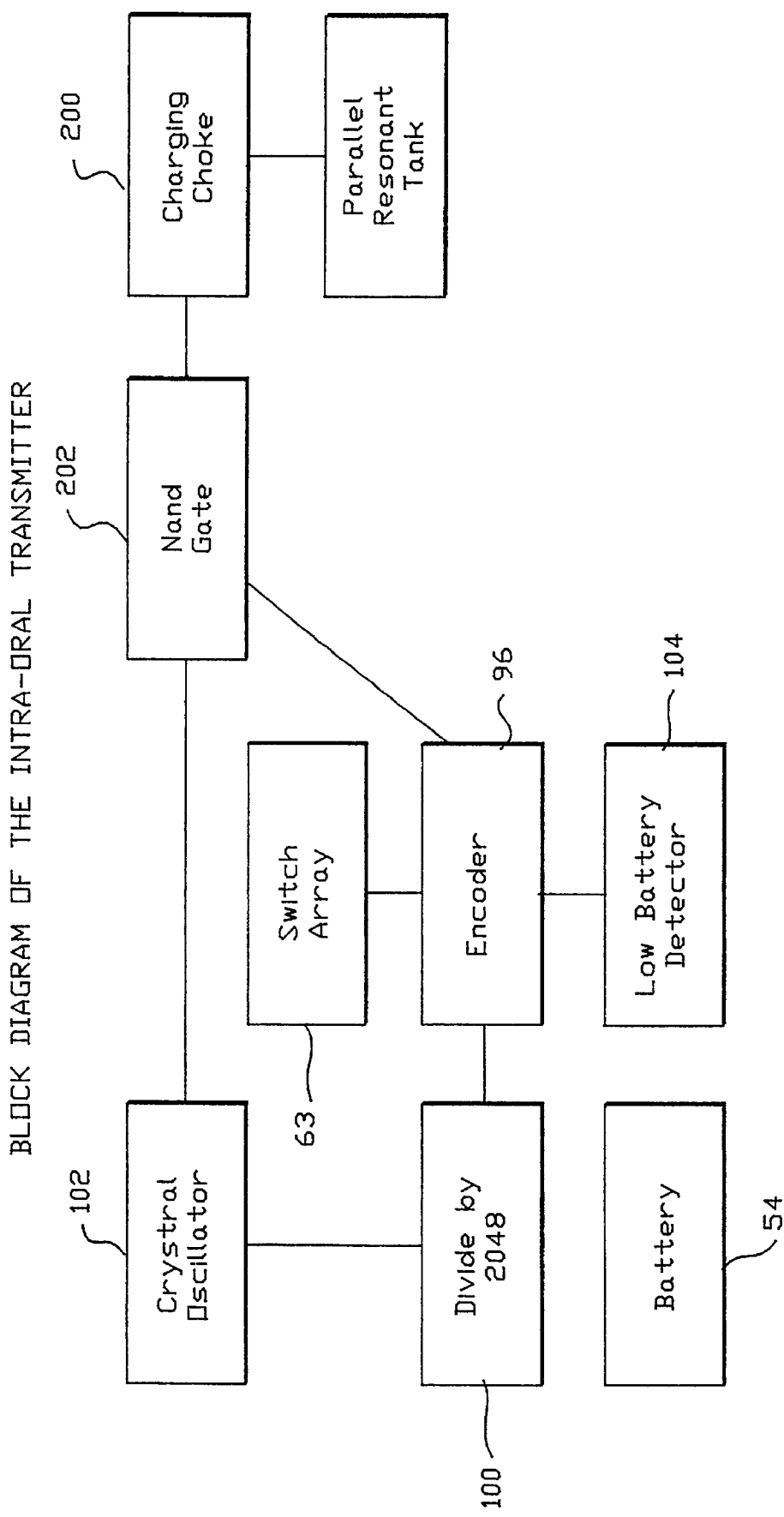
FIG. 17 is a block diagram of the major elements of the alternate intra-oral transmitting assembly for transmission of FIG. 16.
Figure 18:
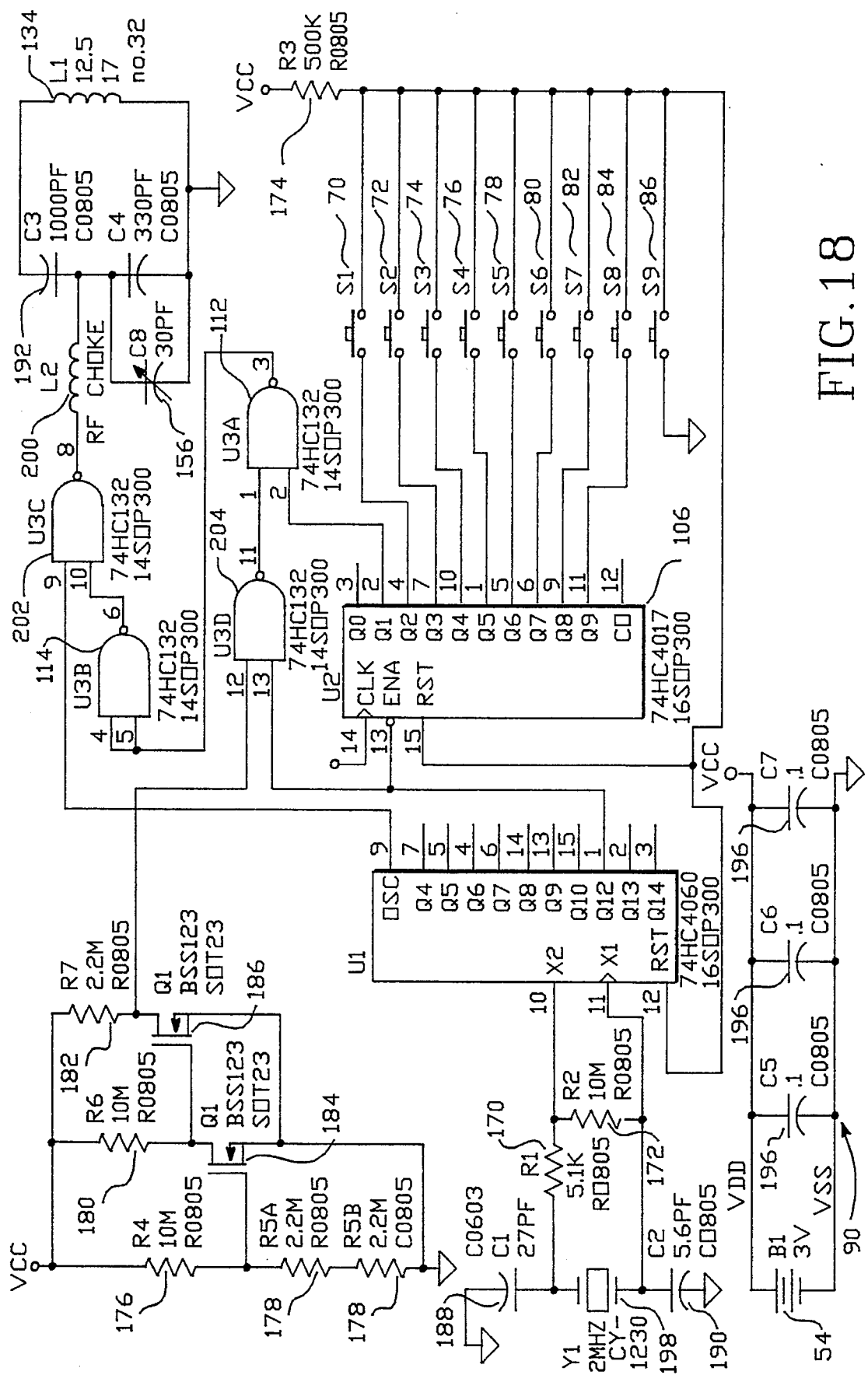
FIG. 18 is an electrical schematic diagram of the alternate intra-oral transmitting assembly of FIG. 16.
Figure 19A:
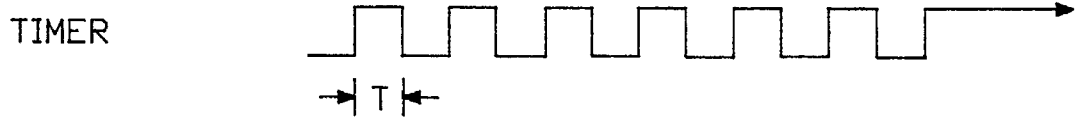
FIG. 19 is a timing diagram of the alternate intra-oral transmitting assembly of FIG. 16 depicting normal battery voltage operation.
Figure 19B:
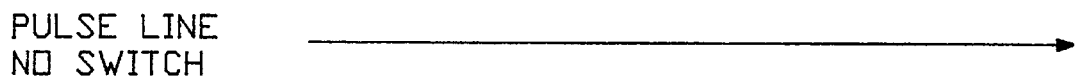
Figure 19C:
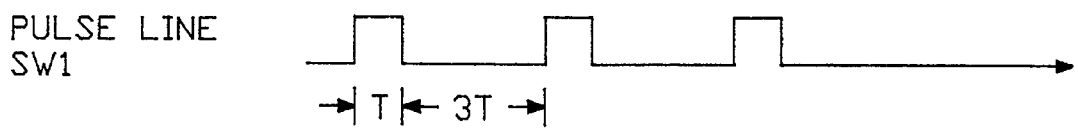
Figure 19D:
Figure 19E:
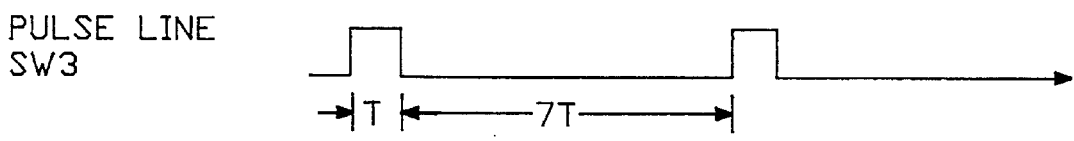
Figure 19F:
Figure 20A:
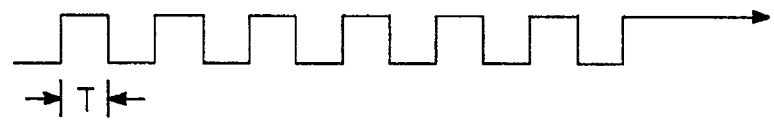
FIG. 20 is a timing diagram of the alternate intra-oral transmitting assembly of FIG. 16 depicting low battery voltage operation.
Figure 20B:
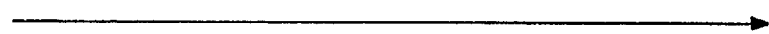
Figure 20C:
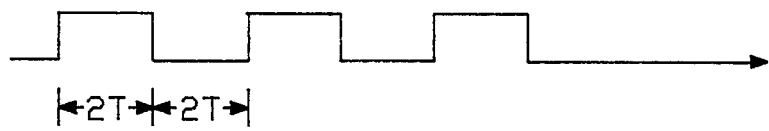
Figure 20D:
Figure 20E:
Figure 20F:
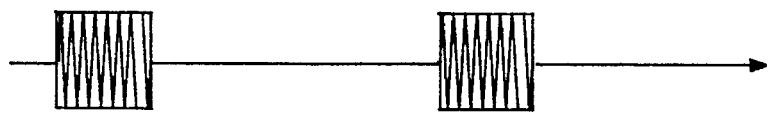

The intra-oral transmitting assembly 12 is shown in block diagram form in FIG. 17 and is shown schematically in FIG. 18 of the drawing.

Electrical power is supplied by a single 3.0 volt battery 54. The negative terminal of battery 54 is connected to the common ground return designated by the inverted triangle symbol. The positive terminal of the battery 54 is distributed to the various circuits shown in FIG. 18. The positive voltage level is designated as VCC.

Battery 54 has bypass capacitors 196 which are connected between the positive and negative terminals of battery 54 and provide bypass for high frequency switching transients.

A keyboard 94 having tongue activatable switches, SW1 70 through SW9 86, is also shown schematically in FIG. 18.

Each of the switches 63 in the preferred embodiment is a momentary, single-pole, single-throw switch having a normally open pair of contacts which are bridged by a conductive key pad member 38 when the switch is activated. Each switch can be activated by tongue depression of the associated nipple 92 which is located on the keyboard membrane 36.

A first contact of each switch contact pair is returned to VCC through the common pullup resistor 174. The resulting signal is biased at the high level when no switch is activated.

The second contact of switches, SW1 70 through SW8 84, is connected to one of the active Q output signals of a decade counter 106, which is a 74HC4017 high-speed CMOS integrated circuit and receives operating power from the battery 54.

The second contact of switch SW9 86 is returned directly to the common ground as shown by the inverted triangle symbol.

The clock input at pin 14 of the decade counter 106 is returned to VCC. When the reset input at pin 15 of the decade counter 106 is at the high level, active output signal Q0 will be ON and the remaining active output signals, Q1 through Q9, of the decade counter 106 will be OFF. Once the reset input is at the low level, the sequencing of the decade counter 106 can begin. The enable input will be used as a clock to advance the state of the decade counter 106.

Timer 100 output signal Q12 is connected to the enable input pin 13 of the decade counter 106. The interval from a high-level-to-low-level transition of the Q12 output signal to the next such transition defines a clock period of the decade counter 106. The state of the decade counter 106 is defined by the level of each of its Q output signals. The state of the decade counter 106 will advance at each high-to-low transition of timer 100 output signal Q12.

The decade counter 106 could more accurately be referred to as a "ring" counter because of its output behavior.

The reason for making a comparison between the decade counter 106 and a "ring" counter is that the active Q output signals of the decade counter 106 are not in binary-coded format, as might be expected. Rather, at each high-to-low transition of timer 100 output signal Q12, the Q1 through Q9 output signals of the decade counter 106 successively turn ON then OFF for one clock period each.

The first time the timer 100 output signal Q12 changes from the high to the low level, the Q0 output signal of the decade counter 106, which has been ON since reset, will turn OFF and the Q1 output signal will turn ON. At the next such transition of the timer 100 output signal Q12, the decade counter 106 output signal Q1 will turn OFF and the output signal Q2 will turn ON, followed by Q3, then Q4, Q5, etc., until the ninth clock pulse, during which decade counter 106 output signal Q9 will be ON.

When a keyboard switch 63 is activated, a specific Q output signal of the decade counter 106 will be connected to the reset input of the decade counter 106 and the reset input of the oscillator 102 and timer 100 through the bridged pair of contacts of the activated switch. The common signal thus formed is returned to VCC through the pullup resistor 174 and comprises a common reset signal. Pullup resistor 174 insures that a high level is present at the reset input of the oscillator 102, timer 100 and decade counter 106 during the time that no keyboard switch 63 is activated. Thus the decade counter 106 always begins its cycle having its Q0 output signal ON and its Q1 through Q9 output signals OFF.

The above description discloses the operation of the decade counter 106 only in general terms. More specifically, the output signals of the decade counter 106 will advance only to the point at which one of the decade counter 106 Q output signals is coupled through the activated keyboard switch 63 back to the common reset input signal.

At that point in the sequence of operation, the decade counter 106 will be reset to its initial state. This action will cause the active Q output signal to return to the low level which will be passed through the activated keyboard switch 63 to the reset input of the oscillator 102, timer 100 and decade counter 106.

Once the common reset signal has returned to the low level, the decade counter 106 will be allowed to resume counting at the next transition of timer 100 output signal Q12 from the high to the low level.

The oscillator 102 and timer 100 are implemented using a high speed, low power CMOS device, the 74HC4060 and receive operating power from the battery 54.

When the common reset signal is at the high level, the oscillator 102 output signal at pin 9 and each of the Q output signals of the timer 100 will be at the low level. As a result, the oscillator 102 and the timer 100 are disabled when no keyboard switch 63 is activated.

The 2.0 Megahertz (hereinafter "MHz") crystal 198 and the biasing network comprised of capacitors 188 and 190 and resistors 170 and 172, are connected to the oscillator 102 X2 and X1 inputs, pin 10 and pin 11 respectively.

When the oscillator 102 is disabled because no keyboard switch 63 is activated, the crystal 198 does not oscillate. This feature permits the intra-oral transmitting assembly 12 to reduce further the current drawn from the battery 54 when no keyboard switch 63 is activated and the oscillator 102 is disabled. The crystal 198 is biased by the biasing network so that upon the reset input changing from the high to the low level, an output signal is available at oscillator 102 pin 9 within approximately one half micro-second. The result of thus disabling the oscillator 102 is an increase in battery life.

The oscillator 102 output signal at pin 9 will be a squarewave having a fundamental frequency of 2.0 MHz when the oscillator 102 is enabled by the activation of any keyboard switch 63.

The timer 100 output signals, Q4 through Q14, are each squarewaves having a fundamental frequency equal to one half that of the next lower numbered output signal. Timer 100 output signal Q4 has a fundamental frequency one sixteenth that of the oscillator 102 output signal at pin 9. Thus timer 100 output signal Q12 at pin 1 will have a fundamental frequency of approximately 0.488 Kilohertz. The period of the squarewave at timer 100 output signal Q12 will be 2.048 millisecond.

If one of the tongue activatable keyboard switches 63 is still depressed, the above described cycle will repeat. The cycle will continue to repeat until all the keyboard switches 63 are released. If a keyboard switch 63 is released during a cycle, the cycle will terminate.

The circuit 104 shown in the upper left corner area of FIG. 18 includes FET's 184 and 186 and resistors 176, 178, 180 and 182. One end of each of the resistors 176, 180 and 182 is connected directly to the positive terminal of the battery 54. Circuit 104 monitors the battery voltage with respect to the common ground return.

The nominal battery voltage is approximately 3.0 volts. If the battery voltage falls below a threshold of approximately 2.0 to 2.2 volts, the circuit 104 will generate a low level output signal. The circuit 104 thus implements the logical compliment of a "low battery detect" function.

If the battery voltage is less than the threshold voltage, the transmitted magnetic field of the intra-oral transmitting assembly 12 will be modified and thus able to communicate the "low battery" status.

In the preferred embodiment, the output signal Q1 of the decade counter 106 will be at the high level for 2.048 millisecond during each cycle of keyboard switch activation. The output signal Q1 of the decade counter 106 is ANDed at NAND gate 204 with the output signal of the "low battery" detect circuit 104.

When the battery voltage exceeds the threshold defined above, the output signal of NAND gate 204 will be the logical compliment of the output signal Q12 of the timer 100. Since the transition from the high to the low level of the output signal Q12 of the timer 100 is used to advance the state of the decade counter 106 and since the output signal of NAND gate 204 is ANDed with the output signal Q1 of the decade counter 106, the output signal of invertor 114 will represent the first 1.024 millisecond of the 2.048 millisecond duration of the output signal Q1 of the decade counter 106.

But when the battery voltage is less than the threshold voltage, the output signal of NAND gate 204 will be at the high level. This circumstance will result in the output signal of invertor 114 being at the high level for the full 2.048 millisecond duration of the output signal Q1 of the decade counter 106.

The output signal of invertor 114 is ANDed with the 2.0 MHz squarewave output signal from the oscillator 102 pin 9. These two signals are ANDed together by NAND gate 202. The output signal of NAND gate 202 drives the resonant circuit comprised of capacitors 192, 194, trimmer capacitor 136 and inductor 134.

RF choke 200 is placed in series between the output signal of NAND gate 202 and the resonant circuit. Choke 200 acts as a charging choke and reduces the current required to charge the resonant circuit by 50 percent, thus helping to further reduce battery drain.

The resonant circuit described above has a resonant frequency of 2.0 MHz. Minor variations in the values of the components of the resonant circuit can be compensated for by adjustment of trimmer capacitor 136.

Inductor 134 is wound within the slot 132 (FIG. 10) at the periphery of the printed circuit board 20 upon which the electronic circuits are mounted. Both the width and depth of the slot 132 as well as the wire gauge of inductor 134 are carefully controlled to reduce the stray capacitance in inductor 134. Such stray capacitance represents additional losses which draw current from the battery 54 not utilized in the generation of the magnetic field.

Inductor 134 is wound in recess 132 around the periphery of the printed circuit board 20, and has 14 turns of no. 32 AWG enameled magnet wire arranged in seven layers of two turns each. The depth of the recess is 0.12 inch and the width of the recess is 0.03 inch.

Because of the manner in which inductor 134 is constructed, the cross-sectional area of inductor 134 is large, resulting in a magnetic field having lower flux density than would a similar inductance wound upon a small ferrite core. Also, careful layout of the components of the electronic assembly 90 upon the PC board 20 further reduces stray capacitance.

There is an advantage which accrues to the use of a magnetic field having lower flux density as is the case in the present invention. That advantage is a decrease in directional sensitivity between the orientation of the intra-oral transmitting assembly 12 and that of the receiver 16.

A typical operation of the intra-oral transmitting assembly 12 will now be described with respect to FIGS. 18, 19 and 20.

When one of the keyboard switches, SW1 70 through SW9 86, is depressed, the magnetic field generated by the current flowing in inductor 134 of the intra-oral transmitting assembly 12 will be a function of the specific keyboard switch activated and also a function of the status of the battery voltage.

The resulting magnetic field (FIG. 19, line "Pulse Line SW1 & Carrier" and line "Pulse Line SW3 & Carrier") will comprise a burst of pulses at the 2.0 MHz rate which is of 1.024 millisecond duration, repeated at intervals dependent upon which switch is activated, when the battery voltage exceeds the threshold voltage. The resulting magnetic field (FIG. 20, line "Pulse Line SW1 & Carrier" and line "Pulse Line SW3 & Carrier") will comprise a burst of pulses at the 2.0 MHz rate and being of 2.048 millisecond duration, repeated at appropriate intervals, when battery 54 has a voltage below the threshold voltage.

Because the "low-battery detect" circuit 104 does not modify the overall length of the cycle, as was discussed above, the repetition rate of the pulsed magnetic field does not change as a function of battery voltage. Only the width of the burst of 2.0 MHz pulses changes, being either 1.024 millisecond or 2.048 millisecond in duration.

Each cycle of the resulting magnetic field can be thought of as being comprised of the burst of 2.0 MHz pulses followed by a period of quiescence equal to a number of intervals of 1.024 millisecond duration which depends upon both the specific keyboard switch activated and the battery voltage.

In example 1, assume the following: the battery voltage exceeds the threshold voltage and switch SW1 70 has been activated. While switch SW1 70 remains activated, the following cycle repeats.

The oscillator 102, the timer 100 and the decade counter 106 are permitted to sequence. The first time the timer 100 output signal Q12 (FIG. 19, TIMER line) moves from the high to the low level, the decade counter 106 output signal Q0 moves from the high to the low level and output signal Q1 turns ON.

The presence of a low level at pin 12 of NAND gate 204 results in the last half of the decade counter 106 output signal Q1 being gated off at the input to pin 10 of NAND gate 202. This circumstance results in the resonant circuit being driven by a burst of 2.0 MHz pulses for a period of 1.024 millisecond At the next transition of the timer 100 output signal Q12 from the high to the low level, the decade counter 106 output signal Q1 turns OFF and output signal Q2 turns ON. This change is coupled through the activated keyboard switch SW1 70 to the reset inputs of the oscillator 102, the countdown 100 and the decade counter 106.

Because the reset inputs to these two integrated circuits operate as asynchronous inputs, the decade counter 106 output signal Q2 returns to the low level within the circuit delay of approximately 80 nanoseconds. The specific pulse width of output signal Q2 of the decade counter 106 is a function of the delay between the reset input and the Q2 output signal of the decade counter and is also a function of stray circuit capacitance and of the battery voltage level. It will be appreciated that the specific pulse width is not critical to the proper operation of the present invention.

The return of the decade counter 106 output signal Q2 to the low level allows the cycle just described to repeat because the common reset signal is at the low level. The cycle will continue to repeat until switch SW1 70 is deactivated. A keyboard switch is deactivated by removing the tongue pressure from the nipple 92 associated with the particular switch.

The cycle which occurs when the battery voltage exceeds the threshold and switch SW1 70 is activated, comprises a burst of 2.0 MHz magnetic pulses having duration of 1.024 millisecond followed by a period of 3.072 millisecond duration of no magnetic pulses. This cycle will repeat if switch SW1 70 continues to be activated.

In example 2, assume the following: the battery voltage is below the threshold voltage and any tongue activated switch 63 has been activated.

The result is the generation of a magnetic field (FIG. 20, line "Pulse Line SW1 & Carrier" and line "Pulse Line SW3 & Carrier") comprising a burst of pulses at the 2.0 MHz rate but of 2.048 millisecond duration. In all other respects, the cycle resulting from activation of keyboard switch SW1 70 when the battery voltage is below the threshold voltage will be identical to the cycle which results when the battery voltage exceeds the threshold voltage. Thus, it is seen that low battery voltage doubles the burst pulse duration and does not change the overall duration of the cycle. The burst pulse width is a function only of the battery voltage while the burst pulse repetition rate is a function of the specific keyboard switch activated (FIG. 19, line "Pulse Line SW1 & Carrier" and FIG. 20, line "Pulse Line SW1 & Carrier").

In a third example, it will be assumed that keyboard switch SW3 74 is activated and that the battery voltage exceeds the threshold voltage. Under these assumptions, the resulting cycle will begin with a 1.024 millisecond burst of 2.0 MHz pulses, followed by an interval of 1.024 millisecond plus 4.096 millisecond of no magnetic field (the duration of the last half of decade counter 106 output signal Q1, plus the cumulative duration of output signals Q2 and Q3, each being 2.048 millisecond in duration), followed by an approximately 80 nanosecond interval of no magnetic field (during which the decade counter 106 output signal Q6 will be at the high level and the oscillator 102, the countdown 100 and the decade counter 106 will be reset). This cycle will continue to repeat so long as keyboard switch SW3 74 is activated.

Thus it will be seen that in the preferred embodiment the cycle of the resulting magnetic field (assuming the battery voltage exceeds the threshold voltage) will be one of the following:

| | |
|---|---|
| SW1 | 1.024 msec burst plus 3 × 1.024 msec quiescence; |
| SW2 | 1.024 msec burst plus 5 × 1.024 msec quiescence; |
| SW3 | 1.024 msec burst plus 7 × 1.024 msec quiescence; |
| SW4 | 1.024 msec burst plus 9 × 1.024 msec quiescence; |
| SW5 | 1.024 msec burst plus 11 × 1.024 msec quiescence; |
| SW6 | 1.024 msec burst plus 13 × 1.024 msec quiescence; |
| SW7 | 1.024 msec burst plus 15 × 1.024 msec quiescence; |
| SW8 | 1.024 msec burst plus 17 × 1.024 msec quiescence; |
| SW9 | 1.024 msec burst plus 19 × 1.024 msec quiescence. |

It will be appreciated that the effects of the approximately 80 nanosecond interval can be safely ignored.

Operation of the intra-oral transmitting assembly 12 is slightly different for keyboard switch SW9 86. As shown in FIG. 18, when activated, keyboard switch SW9 86 connects the reset inputs of the oscillator 102, the timer 100 and the decade counter 106 to the common ground. When keyboard switch SW9 86 is activated, the two integrated circuits are allowed to operate continuously and without reset because no decade counter 106 Q output signal is coupled through the activated keyboard switch to the reset inputs. When the Q9 output signal of the decade counter 106 is ON and the Q12 output signal of the timer 100 is changing from the high to the low level, the Q9 output signal of the decade counter 106 will turn OFF and the Q0 output signal of the decade counter 106 will turn ON. The decade counter 106 will continue to thus cycle through each of its states without reset until the keyboard switch SW9 is deactivated.

Inductor 134 of the resonant circuit of the intra-oral transmitting assembly 12 acts as the primary coil of an air core RF transformer. The secondary coil of this air core RF transformer is located in the receiver 16 which is depicted in block diagram form in FIG. 14.

The present invention relies upon use of the magnetic field produced by a current loop (inductor 134) rather than the electric field radiated from an antenna for coupling the output of the intra-oral transmitting assembly 12 to the receiver 16.

This feature embraces a number of advantages. Among these are (1) use of the relatively small inductor 134 rather than a significantly larger electric field antenna; (2) operation at the relatively low carrier frequency of 2.0 MHz rather than operation at an approximately 88 MHz; (3) use of an AM receiver 16, which in the preferred embodiment is a broadcast band AM receiver modified to operate at the 2.0 MHz carrier frequency; (4) the savings in operating power resulting from the use of the lower carrier frequency, the relatively low duty cycle and the use of the charging choke 200 to drive the resonant circuit; and (5) improvement in non-interference between the output of the intra-oral transmitting assembly 12 and other adjacent transmitting assemblies.

The savings in operating power is a direct result of the use of a low carrier frequency, 2.0 MHz, a low duty cycle and the use of the charging choke 200. The power consumed is a direct, linear function of carrier frequency and stray capacitance. And the use of the charging choke 200 limits the current supplied to the resonant circuit to 50 percent of what the current would be without the choke 200 while producing the same magnetic field strength.

The present invention, by the physical arrangement of the parts in the layout of the printed circuit board 20 and in particular, the arrangement of the inductor 134 in slot 132 at the periphery of the printed circuit board 20, minimizes the stray capacitance, thus further reducing power drawn from the battery.

Earlier designs of intra-oral transmitting assemblies have relied upon use of frequency modulated (FM) transmission at carrier frequencies at or near 88 MHz. The electric field antennas at such frequencies, though quite small, require large amounts of electrical power. The result is a significant decrease in the life of the battery.

The improvement in non-interference of the preferred embodiment results from the fact that the magnetic field strength falls off as the reciprocal of the third power of the distance separating transmitter and receiver. Whereas the electric field strength, relied upon by the existing devices, falls off as the reciprocal of the distance separating transmitter and receiver. Thus when one is able to use the magnetic field rather than the electric field, effective isolation without the need for additional circuitry or shielding is possible over relatively short distances.

It is true that both the electric and the magnetic fields are present in the preferred embodiment when a keyboard switch is activated. However, the tongue activated communications controller 10 uses the air core RF transformer to effectively couple the magnetic field. The invention does not efficiently couple the electric field because no attempt is made to implement an electric field antenna of the necessary size.

The radiated power of the magnetic field, measured at a distance of three meters from the transmitting assembly is approximately 0.25μ Amp/meter.

In the preferred embodiment depicted in FIG. 18 and described above, the preferred battery 54 is a lithium "button" type battery having a 3.0 Volt output level at 30 mAmp-hour. The average current drain using such a battery is less than 0.5μ Amp when no keyboard switches are activated and averages less than 500μ Amp when a keyboard switch is activated. The low battery drain, when no keyboard switch is activated, results in a shelf life for the intra-oral transmitting assembly 12 nearly equal to that of the lithium battery, approximately 10 years.

It is within the scope and spirit of the present invention that the discrete components and the integrated circuits which comprise the electronic assembly 98 can be replaced with a single, custom integrated circuit which is designed to perform the following functions: encoding the activated keyboard switch and battery voltage status into a digital signal; combining the digital signal with a carrier frequency just above the AM broadcast band of frequencies; and generating a magnetic field corresponding to the combined signals for communicating with an AM receiver.

Use of the custom integrated circuit will reduce operating power to approximately 40% of its present value.

The transmitter assembly 90 is easily detachable from the dental appliance. Thus the transmitter assembly 90, including its battery 54 is an easily replaceable, disposable item.

The receiver 16 as implemented in the preferred embodiment of the present invention is a standard AM broadcast band receiver which is modified to permit operation at the 2.0 MHz carrier frequency.

The modifications are (1) change a capacitor value in the local oscillator circuit of receiver 16 to allow the local oscillator to be compatible with the 2.0 MHz carrier frequency, and (2) change the value of a capacitor associated with the ferrite core antenna of the receiver 16 to permit reception of the 2.0 MHz RF magnetic field.

An electrical signal which is output by the modified AM receiver 16 is used as an input to the smart box 18.

The electrical signal as it enters the smart box 18 corresponds to the output of the encoder 96 of the intra-oral transmitting assembly 12. The 2.0 MHz carrier signal has been removed by the demodulation process of receiver 16 and only an equivalent of the digital signal remains.

The smart box 18 is implemented using a standard off-the-shelf programmable micro-controller having microcode and with appropriate interface and support circuits. The demodulated receiver input is fed directly into the programmable micro-controller.

The micro-controller is programmed by means of microcode which includes instructions to the micro-controller to measure the pulse width and pulse repetition rate of the incoming signal. If either parameter is too far outside acceptable limits, the incoming signal is ignored as it may result from interference.

The pulse-width check also allows checking of the status of the intra-oral transmitting assembly 12 battery voltage level. The pulse repetition rate check is used also to determine which of the intra-oral transmitting assembly 12 keyboard switches is activated.

When the activation of a specific keyboard switch is detected by this process, the information is passed to another part of the microcode of the micro-controller. There it is compared with the current state of the system and results in appropriate change of system state or system output.

A concurrent process, operating in the smart box 18 and implemented by a part of the microcode, is constantly displaying the system state to the user, or to operate an audio alarm for the benefit of the visually impaired. In the preferred embodiment, the display is a liquid crystal display of approximately 4 lines of 20 characters each.

Finally, a third concurrent process implemented by the microcode is operating at all times in the programmable micro-controller. That is the interface and control function with external devices.

Depending upon the options installed in the smart box 18, a subprocess of the micro-controller program monitors signals received from, and generates signals and signalling sequences appropriate to communicate with, various devices. Typical devices are depicted in FIG. 14.

Thus the smart box 18 is limited only by the number and type of interfaces provided. Both infra red (IR) and radio frequency (RF) coupling to external devices, as well as direct wired coupling, is understood to be embraced within the scope and spirit of the present invention.

One application which deserves special attention is the typing input to a computer.

Special software is loaded into the computer such that it may be called into operation from the tongue-activated transmitting assembly. A typical operation would be as follows: a top level menu would be displayed to the user upon the smart box 18 display (for example, mounted on the wheelchair as shown in FIG. 15); from this menu of possible applications, the user would activate the tongue activatable keyboard switch which corresponded to the computer application.

Then by depressing a sequence of tongue activatable keyboard switches, the user would bring up the special typing program on the computer with which the user was in communication and control.

In essence, the special program displays a square matrix of sub menus. The user would then activate the keyboard switch corresponding to the sub menu which contains the computer activity he desires to use. This stepping downward through levels of nested menus can be of any desired degree of complexity.

The typing application can be implemented using a 3 by 3 matrix, each sub menu of which is a 3 by 3 matrix. This degree of nesting provides for reaching one of 81 targets and requires a sequence of two tongue activations to reach any target. Each target corresponds to a typing symbol (e.g., the letters of the alphabet, numbers, special symbols and control functions such as backspace, delete, enter, etc.) which may be selected and executed using sequences of two tongue depressions.

The typing application can thus be implemented using an intra-oral transmitting assembly 12 having exactly 9 switches. Other arrangements are clearly possible.

It should be noted that the wheelchair control feature requires a minimum of 9 switches. The nine switches correspond to the following wheelchair commands: forward, forward right, right, backward right, backward, backward left, left, forward left and stop.

While the foregoing detailed description has described several embodiments of the tongue activated communications controller 10 in accordance with this invention, it is to be understood that the above description is illustrative only and not limiting of the disclosed invention. Particularly, any number of devices, including environmental controls, computers, telephone, musicals instruments and other devices could be operated by the tongue activated communications controller 10 in accordance with this invention. It will be appreciated that all such embodiments are within the scope and spirit of this invention. Thus, the invention is to be limited only by the claims as set forth below.

```
( ********************   *************************.   ************
*                                                                  *
*       Tongue Activated Communication Controller Project          *
*                                                                  *
*     FILENAME: LOADTEST.FTH                                        *
*  DESCRIPTION: This module loads all the files which compose       *
*               the Smart Box software as well as some test         *
*               routine used in system evaluation.                  *
*                                                                  *
*               Runs on Prolog STD 7806 Z80 card combined           *
*               with a Prolog 7904 Decoded I/O Utility card.        *
*                                                                  *
*   WRITTEN BY: David Jaffe                                         *
*   START DATE: August 21, 1988                                     *
*    LAST EDIT: December 12, 1988    jeo                            *
*                                                                  *
*******************************************************************)

base @ decimal cr          ." Loading file ASSEMB"        load-file/target c:assemb
13 emit     ." Loading file SERVICE"       load-file/target c:service
13 emit     ." Loading file CLOCK"         load-file/target c:clock
13 emit     ." Loading file TBUTTON"       load-file/target c:tbutton
13 emit     ." Loading file MOUSE"         load-file/target c:mouse
13 emit     ." Loading file CHAIR"         load-file/target c:chair
13 emit     ." Loading file OPTIONS"       load-file/target c:options
13 emit     ." Loading file RESET"         load-file/target c:reset base !
end-of-file
```

```
( ***************************************************************
 *                                                               *
 *       Tongue Activated Communication Controller Project       *
 *                                                               *
 *     FILENAME: LOAD-ALL.FTH                                    *
 *  DESCRIPTION: This module loads all the files which compose   *
 *               the Smart Box software.                         *
 *                                                               *
 *               Runs on Prolog STD 7806 Z80 card combined       *
 *               with a Prolog 7904 Decoded I/O Utility card.    *
 *                                                               *
 *   WRITTEN BY: David Jaffe                                     *
 *   START DATE: July 21, 1988                                   *
 *    LAST EDIT: December 9, 1988    jeo                         *
 *                                                               *
 ***************************************************************)

base @ decimal cr        ." Loading file ASSEMB"      load-file/target a:assemb
13 emit   ." Loading file SERVICE"     load-file/target a:service
13 emit   ." Loading file CLOCK"       load-file/target a:clock
13 emit   ." Loading file BUTTON"      load-file/target a:button
13 emit   ." Loading file MOUSE"       load-file/target a:mouse
13 emit   ." Loading file CHAIR"       load-file/target a:chair
13 emit   ." Loading file OPTIONS"     load-file/target a:options
13 emit   ." Loading file RESET"       load-file/target a:reset base !
end-of-file
```

```
( Assembler definitions, screen 1                      JR09OCT81 )
( Support for the 8085 RIM and SIM have been commented out for Z80 version )
( Added EXAF, EXX,        July 21, 1988)

base @ HEX

VOCABULARY ASSEMBLER IMMEDIATE

VARIABLE OLDBASE
: BEGIN_CODE [COMPILE] ASSEMBLER
        BASE @ OLDBASE !
        HEX
        SP@                                     ;

: CODE CREATE BEGIN_CODE                        ;

ASSEMBLER DEFINITIONS

' BEGIN_CODE CFA  '  ;CODE 8 + !       ( PATCH ';CODE' )
: ?REGISTER DUP 7 SWAP - 0< 19 ?ERROR ;

( OPCODE DEFINING WORDS: )
: TYPE1 <BUILDS , DOES> @ C, ;
: TYPE2 <BUILDS , DOES> @ C, C, ;
: TYPE3 <BUILDS , DOES> @ C, , ;
: TYPE4 <BUILDS , DOES> @ SWAP ?REGISTER SWAP + C, ;
: TYPE5 <BUILDS , DOES> @ SWAP ?REGISTER 8 * + C, ;
: type6 <builds , does> @ , ;     ( for z80 opcodes)

( Assembler definitions, screen 2                      JR09OCT81 )
037 TYPE1 STC,    03F TYPE1 CMC,   000 TYPE1 NOP,   02F TYPE1 CMA,
027 TYPE1 DAA,    0EB TYPE1 XCHG,  0E3 TYPE1 XTHL,  0F9 TYPE1 SPHL,
0E9 TYPE1 PCHL,   0FB TYPE1 EI,    0F3 TYPE1 DI,    076 TYPE1 HLT,
0C9 TYPE1 RET,    0D8 TYPE1 RC,    0D0 TYPE1 RNC,   0C8 TYPE1 RZ,
0C0 TYPE1 RNZ,    0F8 TYPE1 RM,    0F0 TYPE1 RP,    0E8 TYPE1 RPE,
0E0 TYPE1 RPO,    007 TYPE1 RLC,   00F TYPE1 RRC,   017 TYPE1 RAL,
01F TYPE1 RAR,  ( 20 TYPE1 RIM,    030 TYPE1 SIM,  )

0DB TYPE2 IN,     0D3 TYPE2 OUT,   0C6 TYPE2 ADI,   0CE TYPE2 ACI,
0D6 TYPE2 SUI,    0DE TYPE2 SBI,   0E6 TYPE2 ANI,   0EE TYPE2 XRI,
0F6 TYPE2 ORI,    0FE TYPE2 CPI, ( Assembler definitions, screen 3                      JR09OCT81 )
032 TYPE3 STA,    03A TYPE3 LDA,   022 TYPE3 SHLD,  02A TYPE3 LHLD,
0CD TYPE3 CALL,   0DC TYPE3 CC,    0D4 TYPE3 CNC,   0CC TYPE3 CZ,
0F4 TYPE3 CP,     0FC TYPE3 CM,    0EC TYPE3 CPE,   0E4 TYPE3 CPO,
0C3 TYPE3 JMP,    0DA TYPE3 JC,    0D2 TYPE3 JNC,   0CA TYPE3 JZ,
0F2 TYPE3 JP,     0C2 TYPE3 JNZ,   0FA TYPE3 JM,    0EA TYPE3 JPE,
0E2 TYPE3 JPO,    0C4 TYPE3 CNZ, 080 TYPE4 ADD,    088 TYPE4 ADC,   090 TYPE4 SUB,   098 TYPE4 SBB,
0A0 TYPE4 ANA,    0A8 TYPE4 XRA,   0B0 TYPE4 ORA,   0B8 TYPE4 CMP, 0C7 TYPE5 RST,    005 TYPE5 DCR,   004 TYPE5 INR,   003 TYPE5 INX,
00B TYPE5 DCX,    009 TYPE5 DAD,   0C5 TYPE5 PUSH,  0C1 TYPE5 POP,
002 TYPE5 STAX,   00A TYPE5 LDAX, ( Z80 additions to 8080 assembler )
    08    type1    exaf,    ( exchange AF - AF')
    D9    type1    exx,     ( exchange BC - BC'  DE - DE'  HL - HL')
```

```
68ED    type6   inlc,   ( in l,[c])
59ED    type6   outce,  ( out [c],e)
47ED    type6   ldia,   ( ld i,a)
57ED    type6   ldai,   ( ld a,i)
4DED    type6   reti,   ( reti)
45ED    type6   retn,   ( retn)
46ED    type6   im0,    ( im 0)
56ED    type6   im1,    ( im 1)
5EED    type6   im2,    ( im 2)

( Assembler definitions, screen 4                         JR09OCT81 )
: MVI,  ?REGISTER 8 * 6 + C, C, ;
: LXI,  ?REGISTER 8 * 1+ C, , ;
: MOV,  ?REGISTER SWAP ?REGISTER SWAP 8 * + 40 + C, ;

( Register symbols: )
0 CONSTANT B    1 CONSTANT C    2 CONSTANT D    3 CONSTANT E
4 CONSTANT H    5 CONSTANT L    6 CONSTANT M    6 CONSTANT SP
7 CONSTANT A    6 CONSTANT PSW ( Conditional symbols: )
0C2 CONSTANT Z  ( zero )         0CA CONSTANT NZ  ( not zero )
0FA CONSTANT P  ( plus )         0F2 CONSTANT MI  ( minus )
0E2 CONSTANT PE ( even parity)   0EA CONSTANT PO  ( odd parity )
0D2 CONSTANT CY ( carry )        0DA CONSTANT NC  ( no carry )

( Assembler definitions, screen 5                         JR09OCT81 )
: ?CARRY  ( opcode or 1 --- opcode )
    DUP 1 = IF        ( Input is either a conditional jump   )
        DROP 0D2      ( opcode or 1. The 1 comes from the    )
    THEN ;            ( dual use of C for register and carry. )
: IF,     ( opcode --- address )
    ?CARRY C, HERE DUP , ;
: ELSE,   ( address --- address )
    0C3 IF, HERE ROT ! ;
: THEN,   ( address --- )
    HERE SWAP ! ;
: BEGIN,  ( --- address )
    HERE ;
: UNTIL,  ( address, opcode --- )
    ?CARRY C, , ;

( Assembler definitions, screen 6                         JR28DEC81 )

( Updates: The assembler has been modified to include the following  )
( control structures:                                                )
(       BEGIN, ... WHILE, ... REPEAT,          and                   )
(       BEGIN, ... IF,    ... UNTIL-THEN,                            )

: WHILE,      IF, ;
: REPEAT, ( address --- ) SWAP 0C3 C, , THEN, ;
: UNTIL-THEN,   C, SWAP , THEN, ;
: END-CODE ( --- )
    CURRENT @ CONTEXT ! OLDBASE @ BASE !
    SP@ 2 + = IF
        SMUDGE ELSE 1A ERROR
    THEN ;
: NEXT       ( --- )
    0C3 C, NEXT-CODE , ;
```

```
: D-PUSH     ( --- DE-integer, HL-integer )
    0C3 C, NEXT-CODE 2- , ;
: H-PUSH     ( --- HL-integer )
    0C3 C, NEXT-CODE 1- , ;

FORTH DEFINITIONS base !
END-OF-FILE
```

```
(       Tongue Activated Communication Controller Project
  FILENAME:     SERVICE.FTH
  DESCRIPTION:  This module contains assembly language and
                Forth routines that set up the interrupt
                vectors, and the interrupt service routines
                that drive the MacIntosh mouse port, read in
                the TACC serial data, and update the clock.

Runs on Prolog 7806 Z80 card.

WRITTEN BY:   Aleksey Novicov and Robert Berkey
  START DATE:   November 17, 1984
   LAST EDIT:   November 19, 1988      DLJ )

( The 7806 must be reset before this file is reloaded because the  syste
will  crash.  This is likely due to the overwriting of the  clock  interrup
routine,  i.e, the interrupts cannot be active while setting up the  interrup
processes.)

base @ HEX
20 CONSTANT MAC-PORT       ( output port going to MacIntosh mouse port)
20 CONSTANT TACC-PORT      ( input port of the rcvr signal)
F0 CONSTANT CTC0           ( Z80 counter/timer)
F1 CONSTANT CTC1           ( channel 1 command port)
F2 CONSTANT CTC2           ( channel 2 command port)
F3 CONSTANT CTC3           ( channel 3 command port)
08 CONSTANT CTC-CNT        ( period = 0.512 ms.)
A8 CONSTANT CTC-VCTR       ( CTC interrupt generated vector)

60AA CONSTANT VCTR1        ( vector location for channel 1 interrupt)
60AC CONSTANT VCTR2        ( vector location for channel 2 interrupt)
60AE CONSTANT VCTR3        ( vector location for channel 3 interrupt)

BINARY
11010101 CONSTANT CTC-CMD1    ( command instruction for channel 1)
10110101 CONSTANT CTC-CMD2    ( command instruction for channel 2)
DECIMAL                       ( see p. 3-11 of 7806 User's manual)

VARIABLE CLOCK             ( real-time clock updated in TICKER routine)
VARIABLE MAC-SIGNAL        ( data output to the MacIntosh)
VARIABLE X.SPEED           ( high order byte used as a temporary variable)
VARIABLE Y.SPEED           ( high order byte used as a temporary variable)
VARIABLE X.STATE           ( current state of quadrature channels being)
VARIABLE Y.STATE           ( sent to MAC. Only two lowest bits are sent.)
VARIABLE X.DIRECTION
VARIABLE Y.DIRECTION
VARIABLE SEMAPHORE         ( enable and disable TACC interrupt signal, used b
                             the high level routine to control when the int  ca
                             update the OLD-CLOCK and NEW-CLOCK variables.  On!
                             one byte of the variable is used.)
VARIABLE OLD-CLOCK         ( clock of previous lo>hi TACC transition)
VARIABLE NEW-CLOCK         ( clock of latest lo>hi TACC transition)
VARIABLE CLOCK-FROM        ( like OLD-CLOCK but used within the interrupt servic
                             routine)
VARIABLE CLOCK-TO          ( like NEW-CLOCK but used within the interrupt servic
                             routine)
VARIABLE PREV-LEVEL        ( TACC bit level [hi/lo --> 1/0] on last cloc
                             interrupt, used within the interrupt)
```

```
code    di
        di,
        next
end-code di ( Interrupt service routine for updating clock, reading receiver  [TACC-POR]
level bit, and driving MAC mouse port.)
CODE TICKER
        EI,

PSW PUSH,
        D PUSH,
        H PUSH,

CLOCK LHLD,             ( increment CLOCK variable)
        H INX,
        CLOCK SHLD, TACC-PORT IN,           ( get TACC receiver level)
        CMA,                    ( switch for comparison convenience)
        1 ANI,                  ( clear extraneous bits)
        PREV-LEVEL H LXI,
        M CMP, cy               ( compare the previous data bit with t:
                                  latest one)
        PREV-LEVEL STA,         ( save data bit)
        IF,                     ( if there was a lo>hi transition upda
                                  times-of-occurrence variables)
                CLOCK-TO LHLD,  ( CLOCK-TO @ CLOCK-FROM !)
                CLOCK-FROM SHLD,
                CLOCK LHLD,     ( CLOCK @ CLOCK-TO !)
                CLOCK-TO SHLD,
                SEMAPHORE LDA,  ( test SEMAPHORE for on/off)
                A ANA,          ( test accumulator and set comparison bits)
                NZ IF,          ( if SEMAPHORE is non-zero pass information
                                  high-level routine)
                        CLOCK-FROM LHLD,        ( CLOCK-FROM @ OLD-CLOCK !)
                        OLD-CLOCK SHLD,
                        CLOCK-TO LHLD,          ( CLOCK-TO @ NEW-CLOCK !)
                        NEW-CLOCK SHLD,
                        A SUB,                  ( clears accumulator)
                        SEMAPHORE STA,          ( 0 SEMAPHORE C!)
                                        ( indicate to high-level routine that data i
                                          available - note that changing the SEMAPHOR
                                          from FALSE to TRUE only occurs in the  high
                                          level routine)
                THEN,
        THEN, X.SPEED 1+ LDA,         ( Service x-axis)
        A INR,
        Z IF,   X.SPEED     LDA,
                X.SPEED 1+  STA,
                X.DIRECTION LDA,
                A ANA, Z
                X.STATE LDA,
                IF,     RLC,
                ELSE,   RRC,
```

```
        CTC1 OUT,

1 A MVI,
        CTC1 OUT,

CTC-CMD2 A MVI,
        CTC2 OUT,

CTC-CNT A MVI,
        CTC2 OUT,

60 A MVI,
        LDIA,
        im2,            ( updated)
        EI,
        NEXT
END-CODE ( Initialize variables)
CODE INIT-VAR   ( - )
        0 H LXI,
        X.SPEED SHLD,
        Y.SPEED SHLD,
        CLOCK   SHLD,
        33 A MVI,
        X.STATE STA,
        Y.STATE STA,
        13 A MVI,
        MAC-SIGNAL STA,
        NEXT
END-CODE ( This word starts the clock, initialize interrupts and variables)
: INIT   ( - )
        INIT-VAR
        INIT-INTRPTS    ;

base !
END-OF-FILE
```

```
( ****************************************************************
*                                                                *
*       Tongue Activated Communication Controller Project        *
*                                                                *
*     FILENAME: CLOCK.FTH                                        *
*  DESCRIPTION: This  module  contains  Forth  rountines  that  *
*               provide high level timing capabilities. It uses  *
*               the  CLOCK variable which is maintained  within  *
*               SERVICE.FTH,  and  updated  within  the  TICKER  *
*               interrupt service routine.                       *
*                                                                *
*               Runs on Prolog 7806 Z80 card.                    *
*                                                                *
*   WRITTEN BY: Robert Berkey                                    *
*   START DATE: October 23, 1985                                 *
*    LAST EDIT: October 26, 1985                                 *
*                                                                *
*****************************************************************)

base @ HEX ( Delay for n clock tics, but don't delay more than about 4 seconds, to  avo:
unintentional  hangups. 4 seconds corresponds to about 3500 hex loops in  tn:
Forth.)
: TICS           ( n - )
        CLOCK @ +
        3500 0  DO       DUP CLOCK @
                         - 0<
                         IF      LEAVE
                         THEN
                 LOOP    DROP            ;

( Not as accurate as theoretically possible, but accurate to within 3% and +,
the time of one tic. For this clock rate, a tic is .512 ms)
( Convert msec into clock tics)
: MSEC>TICS      ( msec - tics )
        DUP +                            ;

( Delay for n milliseconds, with limit of 4000 ms )
: MSEC    ( n - )
        DUP +
        DUP 0>  IF      TICS
                ELSE    DROP
                THEN                     ;

( Stall until msec past the given clock-time.  Does not delay more than msec.
: NOT-BEFORE     ( clock-time msec - )
        MSEC>TICS   SWAP OVER +    CLOCK @ -    SWAP MIN 0 MAX TICS        ;

base !
END-OF-FILE
```

```
( ****************************************************************
*                                                                *
*       Tongue Activated Communication Controller Project        *
*                                                                *
*       FILENAME: BUTTON.FTH                                     *
*    DESCRIPTION: This  module contains Forth  routines  that    *
*                 interact  with the interrupt  derived  data    *
*                 provided  by  the SERVICE.FTH  routine   to    *
*                 interpret the receiver signal.                 *
*                                                                *
*                 Runs on Prolog 7806 Z80 card.                  *
*                                                                *
*     WRITTEN BY: Robert Berkey                                  *
*     START DATE: October 20, 1985                               *
*      LAST EDIT: October 26, 1985                               *
*                                                                *
******************************************************************)

base @ DECIMAL

VARIABLE KEY-START-TIME              ( set when a key is first pressed)
VARIABLE KEY-DOWN                    ( the key # down since KEY-START-TIME. If th:
                                       value is zero then KEY-START-TIME is n
                                       valid.)
VARIABLE SEMAPHORE-TIME              ( the last time a semaphore was passed)
14 CONSTANT LONGEST-SIGNAL           ( the length of time in milliseconds of  a
                                       signal.  The actual time is closer to  12.
                                       ms, but a more conservative time, about  1
                                       slower,  must  be specified due  to  timi:
                                       inaccuracies. This constant is a  limit
                                       the timing sensitivity of the switch.)

HEX
( Has interrupt driver detected a transition?)
: NEW-DATA?    ( - flag )
      SEMAPHORE C@ 0=                     ;

( Enable next TACC transition signal)
: SEMAPHORE-START    ( - )
      TRUE SEMAPHORE C!
      CLOCK @ SEMAPHORE-TIME !            ;

( Get most recent lo/hi to lo/hi signal in tics)
: DELTA    ( - n )
      NEW-CLOCK @ OLD-CLOCK @ -           ;

( The  following table maps clock tics into the physical switch signal,  f
example  a delta of 5 or 6 tics corresponds with signal 1. Another example:
delta  of  1B  or  1C  tics corresponds with a signal  of  9.   This table  w
determined  by  test.  If the clock interrupt of .512 ms is  changed  for  a
reason this table would have to be recalculated.)

( F E D C  B A 9 8  7 6 5 4  3 2 1 0  -- table headers)
  0 0 0 9  9 0 8 8  0 7 7 6  6 0 5 5
  0 4 4 0  3 3 2 2  0 1 1 0  0 0 0 0    20 TABLE DELTA>SIGNAL ( The  following table provides a convenient remapping between  the  physica
switch signal and the logical switch number)

( 9 8 7  6 5 4  3 2 1  -- table headers)
```

```
       7 4 3   5 9 1   2 6 8   0        0A TABLE SIGNAL>BUTTON

: DELTA>BUTTON   ( delta - button )
       DELTA>SIGNAL
       SIGNAL>BUTTON                    ;

( If n2 is <> 0, change n1 to FALSE)
: ?VALID    ( n1 n2 - 0 if n2 <> 0 )    ( n1 n2 - n1 if n2 = 0 )
       IF      DROP FALSE
       THEN                             ;

( Is there a meaningful delta?)
: DELTA?        ( - delta/0 )
       NEW-DATA?       IF      DELTA
                               SEMAPHORE-START
                               01F OVER U< ?VALID
                       ELSE    FALSE
                       THEN              ;

: BUTTON?       ( -- button/0 )
       DELTA? DUP
       IF      DELTA>BUTTON
       THEN                             ;

( Wait long enough to give the longest signal, 9, a chance to give new dat.
which is expressed as a changed semaphore)
: 9DELAY      ( - )
       SEMAPHORE-TIME @
       LONGEST-SIGNAL NOT-BEFORE        ;

: STILL-PRESSED?       ( button -- button/0 )
       BUTTON? OVER - ?VALID            ;

( Changes KEY-DOWN and KEY-START-TIME if KEY-DOWN different than key/0, not
that a KEY-DOWN value of zero is key not pressed)
: SET-START-TIME       ( key/0 -- key/0 )
       KEY-DOWN @ OVER -
       IF      SEMAPHORE-TIME @ KEY-START-TIME !
               DUP KEY-DOWN !
       THEN                             ;

( Discards potentially stale semaphore data in preparation for r.
examination)
: FRESH-SEMAPHORE      ( - )
       NEW-DATA?       IF      SEMAPHORE-START
                       THEN             ;

( This is a part of the error suppression algorithm. This routine will find
identical valid receiver signal patterns before concluding that a button :
pressed.  These three patterns are spaced apart in time by LONGEST-SIGN/
milliseconds.)
: 3-GOOD-BUTTONS       ( - key/0 )    ( 0 means button not pressed)
       FRESH-SEMAPHORE 9DELAY BUTTON? DUP
       IF      9DELAY STILL-PRESSED? DUP
               IF      9DELAY STILL-PRESSED?
               THEN
       THEN                             ;

( This is the other part of the error suppression algorithm. If this routin
``` does not at first find a good button, it tries three times to find a go
button, before concluding that there is NOT a button pressed. This suppress
falsely concluding that someone has released a button. Ignore up to two fal
no-buttons.)

```
: TACC-KEY?      ( - key/0 )
        3-GOOD-BUTTONS
        ?DUP 0=
        IF      3-GOOD-BUTTONS
        THEN
        ?DUP 0=
        IF      3-GOOD-BUTTONS
        THEN
        SET-START-TIME                  ;
```

( BUTTON driver needs on computer reset, this could be used to initiali.
variables)
```
: INIT-BUTTON   ( - )                   ;
``` base !
END-OF-FILE

```
(       Tongue Activated Communication Controller Project
   FILENAME: TBUTTON.FTH
   DESCRIPTION: This   module  contains  Forth  routines   that
                interact  with  the  interrupt  derived   data
                provided  by  the  SERVICE.FTH  routine    to
                interpret the receiver signal.

Runs on Prolog 7806 Z80 card.

WRITTEN BY: Robert Berkey
   START DATE: October 20, 1985
    LAST EDIT: November 19, 1988 DLJ
    TABLE REV: November 23, 1988  DELTA>SIGNAL-TABLE JEO )

base @ DECIMAL variable vtest

: cr              ( - )    ( create delay)
       1000 0 do loop   cr              ;

: cls             ( - )    ( clear IBM CRT equipped with ANSI.SYS)
       27 emit ." [2J"                  ;

: test?           ( give description of tests)
  cls             1000 0 do loop
       ." TEST1    DELTA            - lo/hi to lo/hi transistion time in tics"
  cr   ." TEST2    BUTTON-SIGNAL-DELTA  - performs table lookups"
  cr   ." TEST3    3-GOOD-BUTTONS   - print button # if 3 identical patterns rec"
  cr   ." TEST4    TACC-KEY?        - print button # after result of 3 attempts"
  cr   ." TOP      Reads DIP switch to re-initialize system parameters"
  cr   ." TEST     Runs current test"
  cr                                    ;

: test1           1 vtest !             ;
: test2           2 vtest !             ;
: test3           3 vtest !             ;
: test4           4 vtest !             ;

: help   test?
         vtest @
         ?dup
         if       ascii 0 +
                  ." Test" emit
         else     ." No test"
         then     ." is active. " cr   ;

VARIABLE KEY-START-TIME              ( set when a key is first pressed)
VARIABLE KEY-DOWN                    ( the key # down since KEY-START-TIME. If thi
                                       value  is  zero then KEY-START-TIME  is  no
                                       valid.)
VARIABLE SEMAPHORE-TIME              ( the last time a semaphore was passed)
28 CONSTANT LONGEST-SIGNAL           ( the  length of time in milliseconds of  a
                                       signal.  The actual time is closer to  12.
                                       ms, but a more conservative time, about  10
                                       slower,  must  be specified  due  to  timin
                                       inaccuracies. This constant is a  limit  o
                                       the timing sensitivity of the switch.)
```

```
HEX
( Has interrupt driver detected a transition?)
: NEW-DATA?    ( - flag )
        SEMAPHORE C@ 0=                ;

( Enable next TACC transition signal)
: SEMAPHORE-START   ( - )
        TRUE SEMAPHORE C!
        CLOCK @ SEMAPHORE-TIME !       ;

( Discards  potentially  stale  semaphore  data  in  preparation  for  ne
examination)
: FRESH-SEMAPHORE       ( - )
        NEW-DATA?       IF      SEMAPHORE-START
                        THEN                   ;

( Get most recent lo/hi to lo/hi signal in tics)
: DELTA    ( - n )
        NEW-CLOCK @ OLD-CLOCK @ -       ;

: ltest cls
        ." DELTA - Lo/hi to lo/hi signal transition time in tics" cr
        fresh-semaphore
        begin   16 0    do      begin   new-data? ?terminal or
                                until
                                ?terminal
                                if      leave
                                else    delta . fresh-semaphore
                                then
                        loop    cr
                ?terminal
        until   key drop cr            ;

: ctable        ( like table, but with characters)
        <builds
                0 do c,
                loop
        does>   + c@                   ;
```

( The  following table maps clock tics into the physical switch  signal, f(
example  a delta of 9 or A tics corresponds with signal 1. Another example:
delta  of  1C or 1D tics corresponds with button 9.  This  table  was
determined  by  test.  If the clock interrupt of .512 ms is  changed or the
button timing is altered, this table would have to be recalculated.)

( 3F 3E 3D 3C 3B 3A 39 38 37 36 35 34 33 32 31 30 -- tics)
  0  0  0  0  0  0  0  0  0  0  0  0  0  9  9
( 2F 2E 2D 2C 2B 2A 29 28 27 26 25 24 23 22 21 20 -- tics)
  0  0  0  8  8  0  0  0  7  7  0  0  0  6  6  0
( 1F 1E 1D 1C 1B 1A 19 18 17 16 15 14 13 12 11 10 -- tics)
  0  0  5  5  0  0  4  4  0  0  0  3  3  0  0  0
( 0F 0E 0D 0C 0B 0A 09 08 07 06 05 04 03 02 01 00 -- tics)
  2  2  0  0  0  1  1  0  0  0  0  0  0  0  0  0  40 CTABLE DELTA>SIGNAL-TAB

40 C-ARRAY DELTA>SIGNAL ( The  following array provides a convenient remapping between  the  physic
switch signal and the logical switch number. The array is initialized on sta
up.)

```
decimal
9 8 7   6 5 4   3 2 1   0    10 CTABLE BOX-TABLE
9 3 8   4 5 1   6 7 2   0    10 CTABLE TONGUE-TABLE

10 C-ARRAY SIGNAL>BUTTON

: box            ( - )    ( install box-table values into array)
       ' box-table 2+          0 signal>button 10 cmove          ;

: tongue         ( - )    ( install tongue-table values into array)
       ' tongue-table 2+       0 signal>button 10 cmove          ;

: DELTA>BUTTON   ( delta - button )
       DELTA>SIGNAL   c@
       SIGNAL>BUTTON  c@                 ;

: 2test cls
       ." BUTTON-SIGNAL-DELTA -"                                                  cr
       ." translated using DELTA>SIGNAL-TABLE and SIGNAL-BUTTON tables"           cr
       ." SIGNAL>BUTTON        DELTA-SIGNAL        DELTA"                         cr
       fresh-semaphore
       begin    5 0 do   begin    new-data? ?terminal or
                         until
                         ?terminal
                         if       leave
                         else     delta dup
                                  delta>signal c@ dup
                                  signal>button c@ . . .  3 spaces
                                  fresh-semaphore
                         then
                loop     cr
                ?terminal
       until    key drop                 ;

( If n2 is <> 0, change n1 to FALSE)
: ?VALID    ( n1 n2 - 0 if n2 <> 0 )      ( n1 n2 - n1 if n2 = 0 )
       IF       DROP FALSE
       THEN                               ;

hex
( Is there a meaningful delta?)
: DELTA?         ( - delta/0 )
       NEW-DATA?        IF       DELTA
                                 SEMAPHORE-START
                                 03F OVER U< ?VALID
                        ELSE     FALSE
                        THEN                      ;

: BUTTON?        ( -- button/0 )
       DELTA? DUP
       IF       DELTA>BUTTON
       THEN                              ;

( Wait long enough to give the longest signal, 9, a chance to give new data
which is expressed as a changed semaphore)
: 9DELAY         ( - )
       SEMAPHORE-TIME @
       LONGEST-SIGNAL NOT-BEFORE         ;

: STILL-PRESSED?         ( button -- button/0 )
```

```
        BUTTON? OVER - ?VALID              ;

( Changes KEY-DOWN and KEY-START-TIME if KEY-DOWN different than key/0, no
that a KEY-DOWN value of zero is key not pressed)
: SET-START-TIME        ( key/0 -- key/0 )
        KEY-DOWN @ OVER -
        IF      SEMAPHORE-TIME @ KEY-START-TIME !
                DUP KEY-DOWN !
        THEN                               ;

( This is a part of the error suppression algorithm.  This routine will find
identical  valid receiver signal patterns before concluding that a  button
pressed.   These  three patterns are spaced apart in  time  by LONGEST-SIGN
milliseconds.)
: 3-GOOD-BUTTONS        ( - key/0 )      ( 0 means button not pressed)
        FRESH-SEMAPHORE 9DELAY BUTTON? DUP
        IF      9DELAY STILL-PRESSED? DUP
                IF      9DELAY STILL-PRESSED?
                THEN
        THEN                               ;

: 3test cls
        ." Test of 3-GOOD-BUTTONS" cr
        begin   3-good-buttons .
                ?terminal
        until   key drop cr                ;

( This is the other part of the error suppression algorithm.  If this  routi
does  not  at first find a good button, it tries three times to  find  a  go
button, before concluding that there is NOT a button pressed. This suppress
falsely concluding that someone has released a button. Ignore up to two  fa
no-buttons.)
: TACC-KEY?     ( - key/0 )
        3-GOOD-BUTTONS
        ?DUP 0=
        IF      3-GOOD-BUTTONS
        THEN
        ?DUP 0=
        IF      3-GOOD-BUTTONS
        THEN
        SET-START-TIME                     ;

: 4test cls
        ." Test of TACC-KEY?" cr
        begin   tacc-key? .
                ?terminal
        until   key drop cr                ;

' 4test         ' 3test         ' 2test         ' 1test         ' noop
5 table tests : test
        vtest @ tests cfa execute          ;

( BUTTON driver initialization)
: INIT  ( - )
        init
        ' delta>signal-table 2+  0 delta>signal   64 cmove
        box
        0 vtest !                          ;
```

```
base !
END-OF-FILE
```

```
( *************************************************************
*                                                              *
*       Tongue Activated Communication Controller Project      *
*                                                              *
*       FILENAME: MOUSE.FTH                                    *
*    DESCRIPTION: This module contains Forth and assembly      *
*                 language routines that perform Macintosh mouse *
*                 emulator functions.                          *
*                                                              *
*                 Runs on Prolog STD 7806 Z80 card combined    *
*                 with a Prolog 7904 Decoded I/O Utility card. *
*                                                              *
*     WRITTEN BY: David Jaffe                                  *
*     START DATE: July 21, 1988                                *
*      LAST EDIT: December 12, 1988   jeo                      *
*                                                              *
***************************************************************)

base @ HEX

21 CONSTANT SPEED-PORT                ( same as MODE-PORT)
VARIABLE LATCH-TIME                   ( in ms, inited to decimal 400 in INIT-MOUSE;
VARIABLE LATCHED                      ( flag to show if center button latched)
VARIABLE ACCELERATED-V-SPEED          ( set within MOUSE, based on dip switch)
VARIABLE VERTICAL-SPEED               ( set within MOUSE, based on dip switch)
VARIABLE ACCELERATED-45-SPEED         ( set within MOUSE, based on dip switch)
VARIABLE 45-DEGREE-SPEED              ( set within MOUSE, based on dip switch)
VARIABLE MS-BEFORE-ACCELERATION       ( inited to 800 ms in INIT-MOUSE)

( Turns mouse button on)
CODE LOWER       ( - )
        MAC-SIGNAL LDA,
        0F ANI,
        MAC-SIGNAL STA,
        NEXT
END-CODE ( Turns mouse button off)
CODE LIFT        ( - )
        MAC-SIGNAL LDA,
        10 ORI,
        MAC-SIGNAL STA,
        NEXT
END-CODE ( Stops mouse moving)
: STOP-MOUSE     ( - )
        0 X.SPEED !     0 Y.SPEED !       ;

( Mapping of speed bits to software velocities)
( Dip switch number:         8 7 6 5 4 3 2 1
  Data bit position:         7 6 5 4 3 2 1 0
  Switch setting:            x x 1 0 1 x x x
  Corresp. speed table entry: column 5)

(  7    6    5    4    3    2    1    0   --> dip switch settings)
FFFF FFFF FEFE FCFC F8F8 F0F0 E0E0 C0C0    8 TABLE BITS>ACCELERATED-V-SPEED
FFFF FEFE FCFC F8F8 F0F0 E0E0 C0C0 8080    8 TABLE BITS>VERTICAL-SPEED
FFFF FEFE FCFC F8F8 F0F0 E0E0 C0C0 8080    8 TABLE BITS>ACCELERATED-45-SPEED
```

```
FDFD FCFC F8F8 F0F0   E0E0 C0C0 8080 4040    8 TABLE BITS>45-DEGREE-SPEED ( Read dip and set speed variables)
: SET-SPEEDS      (  )
        SPEED-PORT P@ -3 ROTATE   7 AND
        DUP BITS>ACCELERATED-V-SPEED     ACCELERATED-V-SPEED !
        DUP BITS>VERTICAL-SPEED          VERTICAL-SPEED !
        DUP BITS>ACCELERATED-45-SPEED    ACCELERATED-45-SPEED !
            BITS>45-DEGREE-SPEED         45-DEGREE-SPEED !           ;

( Has enough time passed?)
: ACCELERATE?    ( - flag )
        CLOCK @ KEY-START-TIME @ -
        MS-BEFORE-ACCELERATION @ MSEC>TICS >    ;

( Selects one of five speeds)
( 0 corresponds to no speed
  1 corresponds to a 45-degree speed
  2 corresponds to a vertical or horizontal speed)
: GET-SPEED      ( 0/1/2 -- speed )
        DUP 0=  IF      DROP 0                   ( stopped)
                ELSE    1 =
                        IF      ACCELERATE?      ( 45-degree)
                                IF      ACCELERATED-45-SPEED
                                ELSE    45-DEGREE-SPEED
                                THEN
                        ELSE    ACCELERATE?      ( vertical or horizontal)
                                IF      ACCELERATED-V-SPEED
                                ELSE    VERTICAL-SPEED
                                THEN
                        THEN    @
                THEN                             ;

( Move mouse at fixed speed in specified direction)
: MAC-DIRECTION          ( create: x-speed-type y-speed-type x-dir y-dir - )
                         ( run: - )
        <BUILDS C,       ( store y-dir)
                C,       ( store x-dir)
                , ,      ( save speed-types)
        DOES>   COUNT Y.DIRECTION C!    COUNT X.DIRECTION C!
                DUP @ GET-SPEED Y.SPEED !
                2 + @ GET-SPEED X.SPEED !        ;

( X-SPEED-TYPE    Y-SPEED-TYPE        X-DIR     Y-DIR)
        0               2              -1         1      MAC-DIRECTION NORTH
        0               2              -1         0      MAC-DIRECTION SOUTH
        2               0               1        -1      MAC-DIRECTION WEST
        2               0               0        -1      MAC-DIRECTION EAST
        1               1               1         1      MAC-DIRECTION NW
        1               1               0         1      MAC-DIRECTION NE
        1               1               0         0      MAC-DIRECTION SE
        1               1               1         0      MAC-DIRECTION SW ( Time this key down)
: KEY-DURATION   ( - tics )
        CLOCK @ KEY-START-TIME @ -       ;

( Check to see if enough time has passed to set the LATCHED flag )
: ?LATCH         ( - )
        KEY-DURATION    LATCH-TIME @ MSEC>TICS
```

```
        SWAP U< IF      TRUE LATCHED !
                THEN                            ;

( Clear the LATCHED flag )
: UNLATCH       ( - )
        FALSE LATCHED !                         ;

( At first clear the LATCHED flag, then depress the mouse button, then watch
the clock as long as the button is pressed.  If enough time has passed then
set the LATCHED flag, otherwise leave it clear.  This permits the quick doub
clicks necessary for Macintosh operation. )
( Control mouse center button)
: LATCH         ( - )
        UNLATCH LOWER
        BEGIN   TACC-KEY? 5 =
        WHILE   ?LATCH
        REPEAT
        LATCHED @ 0=
        IF      LIFT
        THEN                                    ;

decimal
' SE.    ' SOUTH         ' SW     ' EAST          ' LATCH
' WEST   ' NE            ' NORTH  ' NW            ' NOOP  10 TABLE >MOUSE : RUN-MOUSE     ( key - )
        >MOUSE CFA EXECUTE                      ;

( Highest level mouse routine.  When there is no key to service, this routine
returns to the master loop. )
: MOUSE         ( - )
        SET-SPEEDS
        BEGIN   TACC-KEY? ?DUP
        WHILE   RUN-MOUSE
        REPEAT
        STOP-MOUSE                              ;

( Initialization needs of MOUSE driver)
: INIT-MOUSE    ( - )
        400 LATCH-TIME !
        700 MS-BEFORE-ACCELERATION !
        STOP-MOUSE                              ;

base !
END-OF-FILE
```

```
( *****************************************************************
*                                                                 *
*         Tongue Activated Communication Controller Project       *
*                                                                 *
*       FILENAME: CHAIR.FTH                                       *
*    DESCRIPTION: This  module  contains  Forth  routines  that   *
*                 perform  high level DUFCO wheelchair interface  *
*                 functions.                                      *
*                                                                 *
*                 Runs on Prolog 7806 Z80 card.                   *
*                                                                 *
*     WRITTEN BY: Robert Berkey                                   *
*     START DATE: October 24, 1985                                *
*      LAST EDIT: October 26, 1985                                *
*                                                                 *
******************************************************************)

base @ HEX
21 CONSTANT DUFCO-PORT    ( Output port number of the DUFCO relays)

( The following four constants are bit positions within port 21)
8 CONSTANT FORWARD-BIT
2 CONSTANT REVERSE-BIT
1 CONSTANT LEFT-BIT
4 CONSTANT RIGHT-BIT : CHAIR-DIRECTION         ( create: direction-bits - )
                          ( run: - )
        <BUILDS DUP 100 * OR ,   ( dup bits into hi byte and store)
        DOES>   @ DUFCO-PORT P!          ;

FORWARD-BIT                     CHAIR-DIRECTION FORWARD
FORWARD-BIT LEFT-BIT OR         CHAIR-DIRECTION FORWARD-LEFT
LEFT-BIT                        CHAIR-DIRECTION LEFT
REVERSE-BIT LEFT-BIT OR         CHAIR-DIRECTION REVERSE-LEFT
REVERSE-BIT                     CHAIR-DIRECTION REVERSE
REVERSE-BIT RIGHT-BIT OR        CHAIR-DIRECTION REVERSE-RIGHT
RIGHT-BIT                       CHAIR-DIRECTION RIGHT
FORWARD-BIT RIGHT-BIT OR        CHAIR-DIRECTION FORWARD-RIGHT
0                               CHAIR-DIRECTION STOP-CHAIR decimal
' REVERSE-RIGHT         ' REVERSE               ' REVERSE-LEFT
' RIGHT                 ' STOP-CHAIR            ' LEFT
' FORWARD-RIGHT         ' FORWARD               ' FORWARD-LEFT
' NOOP                  10 TABLE >CHAIR : RUN-CHAIR     ( key -- )
        >CHAIR CFA EXECUTE              ;

( Iterate until key-not-pressed)
: CHAIR    ( - )
        BEGIN   TACC-KEY? ?DUP
        WHILE   RUN-CHAIR
        REPEAT  STOP-CHAIR              ;

( Initialization needs for CHAIR)
: INIT-CHAIR    ( - )
        STOP-CHAIR                      ;
```

```
base !
END-OF-FILE
```

```
( ***************************************************************
*                                                                *
*         Tongue Activated Communication Controller Project      *
*                                                                *
*     FILENAME: OPTIONS.FTH                                      *
*  DESCRIPTION: This   module  contains  Forth  routines   that  *
*               provide development options.                     *
*                                                                *
*               Runs on Prolog 7806 Z80 card.                    *
*                                                                *
*   WRITTEN BY: Robert Berkey                                    *
*   START DATE: October 23, 1985                                 *
*    LAST EDIT: October 26, 1985                                 *
*                                                                *
***************************************************************)

base @ decimal
( Use the switch pattern for the test box with the push button and  continuou
switches substitute data table with alternate mapping.  Use DIP switches 7 an
8 to control switch mapping.)

: BOX-SWITCHES            ( - )
        ' BOX-TABLE    2+         0 SIGNAL>BUTTON   10 CMOVE        ;

( Use tongue switch pattern)
: TONGUE-SWITCHES         ( - )
        ' TONGUE-TABLE  2+        0 SIGNAL>BUTTON   10 CMOVE        ;

( Mapping of switch-type bits )
( Dip switch number:          8 7 6 5 4 3 2 1
  Data bit position:          7 6 5 4 3 2 1 0
  Switch setting example:     0 1 x x x x x x
  Corresponding switch:           TONGUE       )

' NOOP                    ( 3)   ' NOOP          ( 2)
' TONGUE-SWITCHES         ( 1)   ' BOX-SWITCHES  ( 0)     4 TABLE >SWITCH ( Map physical signal to logical button depending on DIP switch settings.)
hex
21 CONSTANT MODE-PORT
: MAP-SWITCH     ( signal - button )
        MODE-PORT P@
        -6 ROTATE 3 AND
        >SWITCH CFA EXECUTE            ;

base !
end-of-file
```

```
(       Tongue Activated Communication Controller Project

FILENAME:    RESET.FTH
   DESCRIPTION: This module contains the top level Forth
                routines and initializations to be executed on
                power-up.

Runs on Prolog 7806 Z80 card.

WRITTEN BY:  Robert Berkey
   START DATE:  October 24, 1985
    LAST EDIT:  November 19, 1988        DLJ  )

base @ decimal ( Mapping of mode bits to controlled device )
( Dip switch number:    8 7 6 5 4 3 2 1
  Data bit position:    7 6 5 4 3 2 1 0
  Switch setting:       x x x x x 0 1 0
  Corresponding mode:           CHAIR         )

' NOOP   ( 7)   ' NOOP  ( 6)    ' NOOP  ( 5)   ' NOOP   ( 4)
' NOOP   ( 3)   ' CHAIR ( 2)    ' MOUSE ( 1)   ' HELP   ( 0)    8 TABLE MODES ( Reads the three lowest order bits at the mode-port and execute that mode.)
: RUN-MODES    ( - )
        MODE-PORT P@ 7 AND MODES CFA EXECUTE    ;

( Do what is needed to prepare ram, ports, interrupts, start clock ticking,
etc.)
: INITS    ( - )
        INIT
        INIT-MOUSE
        INIT-CHAIR                              ;

( The last routine loaded into the application, executed at power-up.)
: TOP      ( - )
        INITS
        BEGIN   map-switch
                RUN-MODES
                ?TERMINAL
        UNTIL   KEY DROP cr                     ;

base !
END-OF-FILE
```

What is claimed is:

1. An intraoral tongue activated communications controller comprising:

an input unit having a plurality of user tongue selectable inputs;

an encoder connected to the plurality of user selectable inputs, the encoder producing a first encoded signal corresponding to the user selectable input activated; and a transmitting unit for receiving the first encoded signal as an input and transmitting a second encoded signal with a carrier signal as a low frequency amplitude modulated flux field signal which is emitted by an inductor having an inductance between about 2.8 and 10 μH by the passage of current through the inductor.

2. A controller according to claim 1, wherein the flux field signal has a frequency of about 2 MHz.

3. A controller according to claim 1, wherein the inductor is an air core inductor.

4. A controller according to claim 3, wherein the air core inductor is formed of a wire coil positioned around the periphery of the input unit.

5. A controller according to claim 1, wherein the controller further includes an RF choke, the encoder sending the first encoded signal through the RF choke to the transmitting unit.

6. A controller according to claim 1, wherein the first and second encoded signals are pulsed signals.

7. A controller according to claim 6, wherein the first and second encoded signals include a different pulsed signal corresponding to each user selectable input.

8. A tongue activated communication controller system comprising:

an intraoral tongue activated communications controller, the controller including an input unit having a plurality of user tongue selectable inputs, an encoder connected to the plurality of user selectable inputs, the encoder producing a first encoded signal corresponding to the user selectable input activated, and a transmitting unit for receiving the first encoded signal as an input and transmitting a second encoded signal with a carrier signal as a low frequency amplitude modulated flux field signal which is emitted by a first inductor having an inductance between about 2.8 and 10 μH by the passage of current through the first inductor;

a receiving unit external to the oral cavity including a second inductor for receiving the amplitude modulated flux field signal; and a processing unit for processing the received amplitude modulated flux field signal and producing a command signal corresponding to the user selectable input activated.

9. A controller system according to claim 8, wherein the flux field signal has a frequency of about 2 MHz.

10. A controller system according to claim 8, wherein the first and second inductors are air core inductors which combine to form an air core RF transformer.

11. A controller system according to claim 10, wherein the first inductor is formed of a wire coil positioned around the periphery of the input unit.

12. A controller system according to claim 8, wherein the controller further includes an RF choke, the encoder sending the first encoded signal through the RF choke to the transmitting unit.

13. A controller system according to claim 8, wherein the first and second encoded signals are pulsed signals.

14. A controller system according to claim 13, wherein the first and second encoded signals include a different pulsed signal corresponding to each user selectable input.

15. A controller system according to claim 8, wherein the receiving unit includes an input connected to the second inductor for receiving the amplitude modulated flux field signal;

a filter which filters out the carrier signal from the received amplitude modulated flux field signal to produce a received encoded signal, and an output connected to the filter on which the received encoded signal is placed.

16. A controller system according to claim 15, wherein the processing unit is a computer having, an input connected to the filter output for receiving the received encoded signal, a program unit operating on the received encoded signal to generate a command signal corresponding to each corresponding received encoded signal, and a computer output on which the command signals are placed.

17. A controller system according to claim 16, wherein the program unit includes a plurality of routines which generate a plurality of command signals for controlling a plurality of devices.

18. An intraoral tongue activated communications controller comprising:

an input unit having a plurality of user selectable inputs;

an encoder connected to the plurality of user selectable inputs, the encoder producing a first encoded signal corresponding to the user selectable input activated;

a transmitting unit for receiving the first encoded signal as an input and transmitting a second encoded signal with a carrier signal as a low frequency amplitude modulated flux field signal which is emitted by an inductor having an inductance between about 2.8 and 10 μH by the passage of current through the inductor;

a battery for providing current to pass through the inductor to generate the amplitude modulated flux field signal; and a battery level detector for detecting the voltage level of the battery.

19. A controller according to claim 18, wherein the battery level detector causes the transmitting unit to modify the amplitude modulated flux field signal generated when the voltage level of the battery is below a threshold level.

20. A controller according to claim 19, wherein the battery level detector causes the transmitting unit to generate a signal indicating the voltage level of the battery is below the threshold level.

21. A controller according to claim 19, wherein the battery level detector is an input to the encoder.

* * * * *